United States Patent [19]

Hamprecht et al.

[11] Patent Number: 5,959,116
[45] Date of Patent: *Sep. 28, 1999

[54] PYRIDINE-2, 3-DICARBOXIMIDES THEIR PREPARATION AND THEIR USE FOR CONTROLLING UNDESIRED PLANT GROWTH

[75] Inventors: Gerhard Hamprecht, Weinheim; Peter Münster, Neulussheim; Matthias Gerber, Limburgerhof; Helmut Walter, Obrigheim; Karl-Otto Westphalen, Speyer, all of Germany

[73] Assignee: BASF Aktiengesellschaft, Ludwigshafen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/683,563

[22] Filed: Jul. 12, 1996

Related U.S. Application Data

[62] Division of application No. 08/361,561, Dec. 22, 1994, Pat. No. 5,571,774.

[51] Int. Cl.$^6$ .................... C07D 213/61; C07D 213/72; C07D 213/74
[52] U.S. Cl. .................. 546/310; 546/257; 546/270.4; 546/271.1; 546/271.4; 546/272.1; 546/275.4; 546/276.4; 546/281.4; 546/283.4; 546/286; 546/287; 546/292; 546/294; 546/295; 546/296; 546/297; 546/304; 546/309; 546/311; 546/312; 546/321

[58] Field of Search ................... 546/310, 297, 546/341, 342, 268.4, 268.7, 269.1, 269.4, 269.7, 270.4, 311, 309, 321, 292, 294, 295, 296, 287

[56] References Cited

U.S. PATENT DOCUMENTS

| | | | |
|---|---|---|---|
| 5,252,538 | 10/1993 | Cross | 504/156 |
| 5,262,384 | 11/1993 | Hamprecht | 504/225 |

OTHER PUBLICATIONS

Tominaga Y. et al. J. Heterocyclic Chem. 30, pp. 267–273, Jan. 1993.
Sarges R et al., J. Med. Chem. 33(7), 1859–65, 1990.
Nagano H et al., Yakugaku Zasshi, 106(10), 872–7, 1986.

*Primary Examiner*—Evelyn Mei Huang
*Attorney, Agent, or Firm*—Keil & Weinkauf

[57] ABSTRACT

A pyridine-2,3-dicarboxylic acid diester of the formula Va

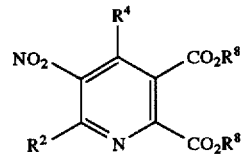

where the radicals $R^2$ and $R^4$ have the meanings set out in the specification and where $R^8$ is a $C_1$–$C_4$-alkyl, $C_3$–$C_5$-alkenyl or $C_3$–$C_5$-alkynyl radical, which may be substituted by halogen, phenyl or $C_1$–$C_4$-alkoxy.

3 Claims, No Drawings

PYRIDINE-2,3-DICARBOXIMIDES THEIR PREPARATION AND THEIR USE FOR CONTROLLING UNDESIRED PLANT GROWTH

This is a Division of application Ser. No. 08/361,561, filed Dec. 22, 1994 U.S. Pat. No. 5,571,774.

BACKGROUND OF THE INVENTION

1. Field of the Invention

The present invention relates to pyridine-2,3-dicarboximides of the general formula I

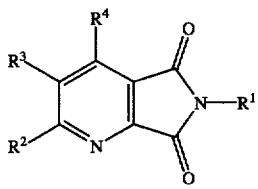

where
R$^1$ is
hydrogen;
C$_1$–C$_4$-alkoxy;
C$_1$–C$_6$-alkyl which can carry one to three of the following groups: C$_1$–C$_4$-alkoxy, C$_1$–C$_4$-haloalkoxy, C$_1$–C$_4$-alkylthio, C$_1$–C$_4$-haloalkylthio, C$_1$–C$_4$-dialkylamino, C$_3$–C$_8$-cycloalkyl, halogen, excluding C$_1$–C$_4$-dialkylaminoethyl if one of the radicals R$^2$, R$^3$ or R$^4$ is amino or hydroxyl;

C$_3$–C$_8$-cycloalkyl, which can carry one to three of the following groups: C$_1$–C$_6$-alkyl, C$_1$–C$_6$-haloalkyl, C$_1$–C$_4$-alkoxy, C$_1$–C$_4$-haloalkoxy, halogen or nitro;

C$_3$–C$_6$-alkenyl or C$_3$–C$_6$-alkynyl, which can be substituted up to three times by halogen, and at least one radical R$^2$, R$^3$ or R$^4$ is nitro, a group OR$^5$ or a group NR$^6$R$^7$ and the other radicals R$^2$, R$^3$ and R$^4$ are defined as follows:

i) hydrogen;
ii) halogen, nitro or cyano;
iii) C$_1$–C$_6$-alkyl, which can be substituted by one to five halogen atoms and/or one or two of the following radicals:
C$_1$–C$_4$-alkoxy, C$_1$–C$_4$-haloalkoxy, C$_1$–C$_4$-alkylthio, C$_1$–C$_4$-haloalkylthio, C$_3$–C$_6$-cycloalkyl or cyano;
iv) benzyl which can be substitute d up to three times by C$_1$–C$_4$-alkyl, C$_1$–C$_4$-haloalakyl, C$_1$–C$_4$-alkoxy, C$_1$–C$_4$-haloalkoxy, C$_1$–C$_4$-alkylthio, C$_1$–C$_4$-haloalkylthio, halogen, cyano or nitro;
v) C$_3$–C$_8$-cycloalkyl which can be substituted one to three times by C$_1$–C$_4$-alkyl or halogen;
vi) C$_2$–C$_6$-alkenyl which can be substituted up to three times by halogen and/or once by C$_1$–C$_3$-alkoxy or by phenyl which can carry one to three of the following groups: C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$-haloalkylthio, halogen, cyano or nitro;
vii) C$_2$–C$_6$-alkynyl which can be substituted up to three times by halogen or C$_1$–C$_3$-alkoxy and/or once by phenyl which can carry one to three of the following groups: C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$-haloalkylthio, halogen, cyano or nitro;
viii) C$_1$–C$_4$-alkoxy, C$_1$–C$_4$-alkylthio, C$_1$–C$_4$-haloalkoxy, C$_1$–C$_4$-haloalkylthio, C$_2$–C$_5$-alkenyloxy, C$_2$–C$_5$-alkynyloxy, C$_1$–C$_4$-alkylsulfinyl, C$_1$–C$_4$-alkylsulfonyl, C$_1$–C$_4$-haloalkylsulfonyl;
ix) phenoxy or phenylthio which can be substituted up to three times by C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$-haloalkylthio, halogen, cyano or nitro;
x) a 5- or 6-membered heterocyclic radical having one or two heteroatoms selected from the group consisting of oxygen, sulfur and nitrogen which can carry one or two of the following groups: C$_1$–C$_3$-alkyl, halogen, C$_1$–C$_3$-alkoxy or C$_2$–C$_4$-alkoxycarbonyl;
xi) phenyl which can carry one to three of the following groups:
C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio , C$_1$–C$_6$-haloalkylthio, halogen, nitro or cyano;
xii) a group OR$^5$, where R$^5$ is hydrogen, C$_1$–C$_4$-alkylcarbonyl, C$_1$–C$_4$-haloalkylcarbonyl, C$_1$–C$_4$-alkoxycarbonyl, C$_1$–C$_4$-alkoxy-C$_2$-C$_4$-alkoxycarbonyl, C$_1$–C$_4$-alkylcarbamoyl, C$_1$–C$_4$-dialkylcarbamoyl, C$_1$–C$_4$-alkylsulfonyl, C$_1$–C$_4$-haloalkylsulfonyl, sulfamoyl, C$_1$–C$_4$-alkylaminosulfonyl, C$_1$–C$_4$-dialkylaminosulfonyl, phenylsulfonyl, which can be substituted one to three times by C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, halogen, cyano or nitro;
xiii) a group NR$^6$R$^7$, where R$^6$ is hydrogen, C$_1$–C$_4$-alkyl, benzyl, C$_1$–C$_4$-alkoxy or, together with R$^7$, is C=S and R$^7$ is hydrogen, C$_1$–C$_4$-alkyl, C$_1$–C$_4$-alkylcarbonyl, C$_1$–C$_4$-haloalkylcarbonyl, C$_1$–C$_4$-alkoxycarbonyl, C$_1$–C$_4$-alkoxy-C$_2$-C$_4$-alkoxycarbonyl, C$_1$–C$_4$-alkylcarbamoyl, C$_1$–C$_4$-dialkylcarbamoyl, C$_1$–C$_4$-alkylsulfonyl, C$_1$–C$_4$-haloalkylsulfonyl, sulfamoyl, C$_1$-C$_4$-alkylaminosulfonyl, C$_1$–C$_4$-dialkylaminosulfonyl, phenylsulfonyl, which can be substituted one to three times by C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, halogen, cyano or nitro;

excluding $^6$-amino-5-cyano-4-phenylpyridine-2,3-dicarboximide;

and their agriculturally utilizable salts.

The invention furthermore relates to processes for preparing the compounds I and their use for controlling undesired plant growth, and novel pyridine-2,3-dicarboxylic acid esters and pyridine-2,3-dicarboxylic anhydrides, in particular nitro-substituted in each case, which are used as intermediates for preparing the compounds I.

2. Description of Related Art

N-substituted pyridinedicarboximides and their derivatives are known. EP-A 128 006 describes, inter alia, N-cycloalkylenepyridinedicarboximides and their use as soil fungicides.

U.S. Pat. No. 3,539,568 describes a process for preparing 2,3- and 3,4-pyridinedicarboximides and their reaction to give isomeric dicarboxamides which can be used as intermediates for herbicidal pyrimidinediones.

U.S. Pat. No. 4,261,730 describes 3-carboxypyridine-2-N-(aryl)carboxamides and phthalamic acids having growth-regulating action.

U.S. Pat. No. 4,658,030 discloses a process for preparing herbicidal 2-(imidazolin-2-yl)nicotinic acids based on 3-carboxypyridine-2-(N-2-carbamido-3-methyl-2-butyl) carboxamides.

Helv. Chim. Acta 1988, Vol. 71, pp. 486 and 493 discloses a cycloaddition process for preparing pyridine-2,3-dicarboximides.

J 5 7085-386 describes specifically substituted pyridine-2,3-dicarboximides having antitumor action. 6-Amino-5-cyano-4-phenylpyridinecarboximide is disclosed in CA 117, 150 849.

Herbicidally active pyridine-2,3-dicarboximides are disclosed in EP-A 422 456.

Intermediates from the pyridine-2,3-dicarboxylic acid diester group can only be taken from the prior art in isolated cases. Thus EP-A 227 932 describes pyridine-2,3-dicarboxylic acid diesters having the following substitution pattern in the 5/6 position: $CH_3/NO_2$, $NH_2/NH_2$, $NO_2/Cl$ and $NO_2/NH_2$. Dimethyl 4-aminopyridine-2,3-dicarboxylate is known from Chemical Abstracts 111, 112292p (1989), dimethyl or diethyl 5-amino-6-methylpyridine-2,3-dicarboxylate from Beilstein No. 4-22-006875 (Jones, Am. Soc. 74 (1972), p. 1489). Diethyl 5-acetamido- and 5-methylamino-6-methylpyridine-2,3-dicarboxylates are published in EP-A 322 616. 4-Diethylamino-5-methyl- and 5-diethylamino-4-methylpyridine are described in Chemical Abstracts 81, 169499c (1974) and 79, 31999t (1973).

SUMMARY OF THE INVENTION

It is an object of the present invention to make available pyridine-2,3-dicarboximides having improved biological activity, in particular better selectivity or higher herbicidal activity.

We have now found that this object is achieved by the pyridine-2,3-dicarboximides defined at the outset.

DESCRIPTION OF THE PREFERRED EMBODIMENT

Preferred pyridine-2,3-dicarboximides of the formula I are those where $R^1$ is hydrogen, $C_1$–$C_6$-alkyl, $C_3$–$C_6$-alkenyl, $C_3$-$C_6$-alkynyl, 1-(cyclopropyl)-$C_1$–$C_3$-alkyl, 1-$C_1$–$C_2$-alkylcyclopropyl or $C_3$–$C_6$-cycloalkyl and two of the three radicals in the pyridine ring $R^2$, $R^3$ or $R^4$ independently of one another are hydrogen, $C_1$–$C_4$-alkyl which can be substituted by one to five halogen atoms, $C_1$–$C_4$-alkoxy, halogen or cyano, while the third substituent is a nitro group, a group $OR^5$, in particular acetoxy, trifluoroacetoxy or methoxycarbonyl, or a group $NR^6R^7$, in particular amino, methylamino, dimethylamino, acetamido or trifluoroacetamido.

Particularly preferably, at least one of the radicals $R^2$, $R^3$ or $R^4$ is nitro or trifluoroacetamido. Compounds having mono- or disubstitution in the pyridine ring are also preferred. The substituent on the imide nitrogen $R^1$ is preferably an alkyl radical, in particular a branched alkyl radical such as i-propyl, sec-butyl or tert-butyl or a 1-(cycloalkyl)-$C_1$–$C_3$-alkyl radical such as 1-(cyclopropyl)methyl, 1-(cyclopropyl)ethyl or 1-(cyclopropyl)-propyl.

The invention further relates to novel intermediates such as anhydrides and substituted pyridine-2,3-dicarboxylic acid esters. The following compounds can be mentioned here:

pyridine-2,3-dicarboxylic anhydrides of the formulae IIa and IIc

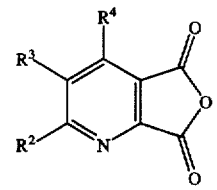

IIa, c where at least one of the radicals $R^2$, $R^3$ or $R^4$ is nitro or $NR^6R^7$, and the other radicals have the meanings mentioned at the outset for the final products I.

Intermediates according to the invention in the dialkyl ester stage are nitro- or amino-substituted dialkyl pyridine-2,3-dicarboxylates of the formulae Va to Vd

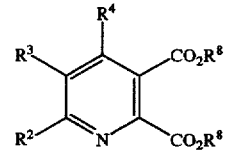

Va-Vd where $R^8$ is a $C_1$–$C_4$-alkyl, $C_3$–$C_5$-alkenyl or $C_3$–$C_5$-alkynyl radical, it being possible for the radicals mentioned to be substituted in each case by halogen, in particular one to three halogen radicals such as fluorine, chlorine or bromine, by $C_1$–$C_4$-alkoxy or by phenyl, and the radicals $R^2$ to $R^4$ have the following meanings:

Va: $R^4$ is a nitro group and the radicals $R^2$ and $R^3$ have the meanings mentioned at the outset, as for the final product I;

Vb: $R^3$ is a nitro group and the radicals $R^2$ and $R^4$ have the meanings mentioned at the outset, as for the final product I, with the proviso that $R^2$ is not methyl, halogen or amino ($NH_2$) if $R^4$ is hydrogen;

Vc: $R^2$ is a nitro group and the radicals $R^3$ and $R^4$ have the meanings mentioned at the outset, as for the final product I;

Vd: the radicals $R^2$, $R^3$ and/or $R^4$ are a group $NR^6R^7$ and the other radicals $R^2$, $R^3$ or $R^4$ have the meanings mentioned at the outset, as for the final product I, excluding diethyl and dimethyl 5-amino-6-methylpyridine-2,3-dicarboxylate, dimethyl 4-aminopyridine-2,3-dicarboxylate, diethyl 5,6-diaminopyridine-2,3-dicarboxylate, diethyl 6-amino-5-nitropyridine-2,3-dicarboxylate, diethyl 5-acetamido-6-methylpyridine-2,3-dicarboxylate, diethyl 5-methylamino-6-methylpyridine-2,3-dicarboxylate, diethyl 4-diethylamino-5-methylpyridine-2,3-dicarboxylate and diethyl 6-diethylamino-5-methylpyridine-2,3-dicarboxylate.

The pyridine-2,3-dicarboximides of the formula I can form addition salts with inorganic acids or with alkyl halides or they can be reacted, if one of the substituents has acidic properties, with inorganic and organic bases to give salts. The corresponding salts are likewise a part of the invention.

Suitable basic salts are eg. those of the alkali metals, preferably the sodium and potassium salts, those of the alkaline earth metals, preferably calcium, magnesium and barium salts, and those of the transition metals, preferably manganese, copper, zinc and iron salts, and also the ammonium salts which can carry one to three $C_1$–$C_4$-alkyl or hydroxy-$C_1$-$C_4$-alkyl substituents and/or a phenyl or benzyl substituent, preferably diisopropylammonium, tetramethylammonium, tetrabutylammonium, trimethylbenzylammonium and trimethyl-(2-hydroxyethyl)ammonium salts, the phosphonium salts, the sulfonium salts, preferably tri-($C_1$-$C_4$)-alkylsulfonium salts, and the sulfoxonium salts, preferably tri-($C_1$-$C_4$)-alkylsulfoxonium salts.

If the substitution pattern on the pyridine-2,3-dicarboximide I leads to optically active compounds, in addition to the racemates the invention also includes the (+) and (−) enantiomers.

The pyridine-2,3-dicarboximides of the formula I can be prepared in various ways, which are described in EP-A 422 456.

According to the invention, pyridine derivatives of the formula I are obtained by reaction of pyridinedicarboxylic anhydrides II

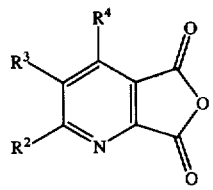

II in an inert organic solvent with a primary amine III (preferably in approximately stoichiometric amounts)

 III to give a pyridinedicarboxylic acid hemiamide IV

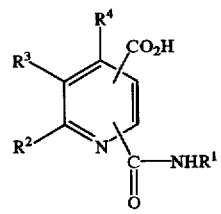

IV and cyclization thereof with dehydrating agents to give I.

Additionally, chemically unique processes have been found for preparing the compounds Ia

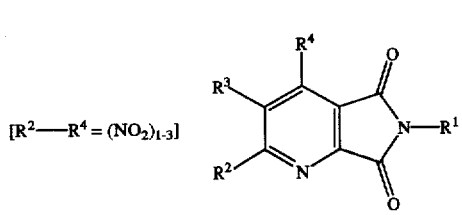

Ia where $R^2$ to $R^4$ have the abovementioned meanings, at least one of the radicals $R^2$ to $R^4$, two of the radicals $R^2$ to $R^4$ or all the radicals $R^2$ to $R^4$ being nitro, by treating pyridine derivatives Ib

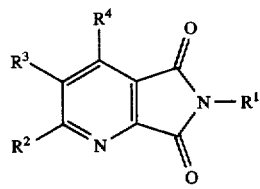

Ib where $R^1$ to $R^4$ have the abovementioned meanings, at least one of the radicals $R^2$ to $R^4$ being hydrogen, or two or all of the radicals $R^2$ to $R^4$ being hydrogen, or the N-oxides of Ib with nitrating agents and if appropriate then removing the N-oxide group.

In the context of the preparation of the compounds according to the invention, it has furthermore been found that pyridine derivatives of the formula Ia are likewise advantageously obtained if the starting materials are pyridinedicarboxylic anhydrides of the formula IIb (or their N-oxides)

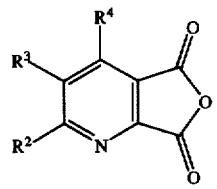

IIb where $R^2$ to $R^4$ have the abovementioned meanings, at least one of the radicals (namely the radical which is replaced by nitro), two of the radicals or all the radicals, $R^2$ to $R^4$, are hydrogen, these are reacted with nitrating agents to give pyridinedicarboxylic anhydrides IIa

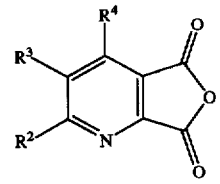

IIa where $R^2$ to $R^4$ have the abovementioned meanings, at least one of the radicals, or two or all the radicals, $R^2$ to $R^4$, being nitro, and this is then converted using a substituted amine, as described, to the pyridine derivatives Ia.

Preparation of the pyridinedicarboxylic acid hemiamides IV is expediently carried out by initially introducing the anhydride II in an inert solvent and adding dropwise approximately molar amounts of an amine III, if appropriate likewise dissolved in an inert solvent. After reaction is complete, the reaction product is filtered off with suction or isolated by concentrating the solvent used, the hemiamides IV being obtained.

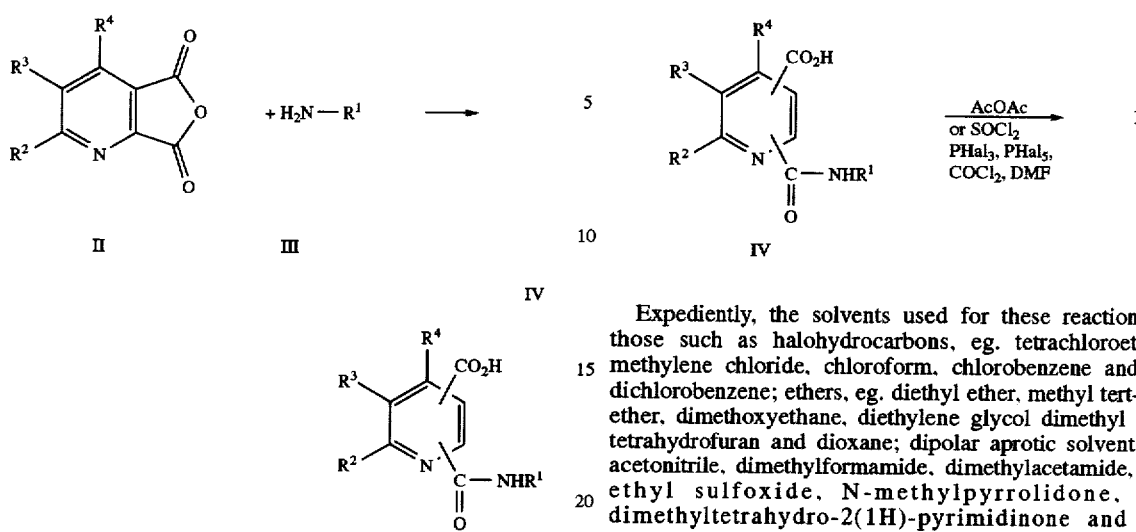

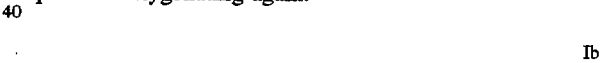

Expediently, the solvents used for these reactions are those such as halohydrocarbons, eg. tetrachloroethane, methylene chloride, chloroform, chlorobenzene and 1,2-dichlorobenzene; ethers, eg. diethyl ether, methyl tert-butyl ether, dimethoxyethane, diethylene glycol dimethyl ether, tetrahydrofuran and dioxane; dipolar aprotic solvents, eg. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolidin-2-one; aromatics, eg. benzene, toluene, xylene, pyridine and quinoline; ketones, eg. acetone, methyl ethyl ketone or appropriate mixtures.

The reaction can be carried out at from −10° C. to the reflux temperature of the particular solvent or mixture, preferably at from −20 to 120° C.

The molar ratios in which the starting compounds required are reacted with one another are preferably from 0.9:1 to 3:1 for the ratio of amine III to anhydride II. The concentration of the starting materials in the solvent is eg. from 0.1 to 5 mol/l, preferably from 0.2 to 2 mol/l.

The pyridinedicarboxylic acids or anhydrides required as starting materials for this process are commercially available, known from the literature or can be prepared by generally known methods. A general survey is found in Beilstein H 22, 150–160, E I 531–536, E II 104–111, H 27, 261, E I 319, E II 299, R. C. Elderfield, Heterocyclic Compounds, Vol. I, Chapt. 8, J. Wiley and Sons, N.Y., E. Klingberg, 'Pyridine and its Derivatives', Part 3, Chapt. X, in The Chemistry of Heterocyclic Compounds, 1962, Interscience Publishers, and in EP-A 299 362 and EP-A 422 456.

The cyclization of the hemiamides IV is carried out by dehydrating using customary dehydrating agents, for example acetic anhydride or inorganic acid halides, such as thionyl chloride, phosgene, phosphorus trichloride or pentachloride, to give the pyridine derivatives of the formula I. The reaction is expediently carried out by initially introducing the carboxamides in an inert organic solvent and adding the dehydrating agent dropwise, if appropriate likewise dissolved in an inert solvent. The mixture can be worked up in the customary manner, for example by hydrolysis with water and filtration with suction or extraction of the product with an organic solvent and concentration of the organic solvent:

Expediently, the solvents used for these reactions are those such as halohydrocarbons, eg. tetrachloroethane, methylene chloride, chloroform, chlorobenzene and 1,2-dichlorobenzene; ethers, eg. diethyl ether, methyl tert-butyl ether, dimethoxyethane, diethylene glycol dimethyl ether, tetrahydrofuran and dioxane; dipolar aprotic solvents, eg. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolidin-2-one; aromatics, eg. benzene, toluene, xylene, pyridine and quinoline; ketones, eg. acetone, methyl ethyl ketone or appropriate mixtures. The reaction can be carried out at from −10° C. to the reflux temperature of the particular solvent, preferably at from 0 to 150a° C.

The molar ratios in which the starting compounds are reacted with one another are in general from 0.9:1 to 5:1 for the ratio of dehydrating agents to acid amide.

The concentration of the starting materials in the solvent (mixture) is in general from 0.1 to 5 mol/l, preferably from 0.2 to 2 mol/l.

A process for preparing compounds Ia where at least one of the radicals $R^2$ to $R^4$ is nitro consists in the treatment of a pyridine derivative Ib with nitrating agents.

The reaction is preferably carried out by treating a pyridine derivative Ib with nitric acid on its own or mixed with sulfuric acid (generally called nitrating acid) and if appropriate deoxygenating again.

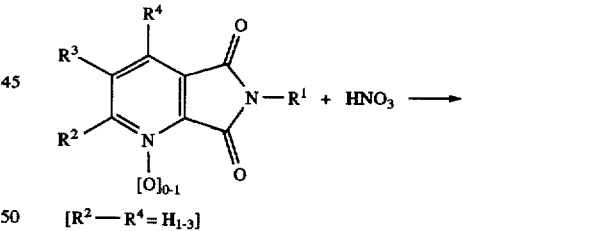

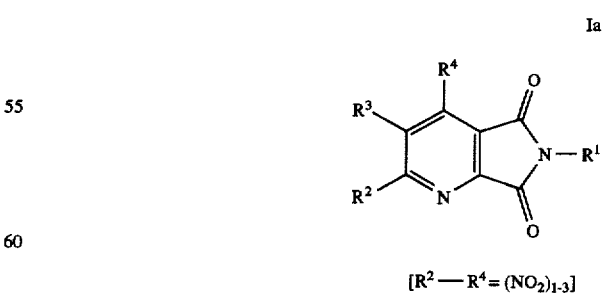

To carry out the nitration, the pyridine derivative Ib can be dissolved or suspended in sulfuric acid and nitric acid or nitrating acid added. Occasionally, it is advantageous to introduce the pyridine derivative Ib in initially introduced nitrating acid or nitric acid. The reaction can be carried out using dilute nitric acid [D: 1.0–1.37), but the use of concentrated to fuming nitric acid [D: 1.37–1.52] is more expedient. If nitrating acid is used, mixtures of eg. 20% nitric acid, 60% sulfuric acid and 20% water up to 45% nitric acid and 55% sulfuric acid are customarily employed.

An increase in the nitrating action is effected by use of mixtures of fuming nitric acid [D: 1.52] with fuming sulfuric acid (oleum). Instead of sulfuric acid, phosphoric acid or liquid hydrogen fluoride can also be used.

Advantageously, the nitration can also be carried out in the presence of glacial acetic acid. To this end, the pyridine derivative Ib is dissolved or suspended in glacial acetic acid and 60 to 100% strength nitric acid is added on its own or diluted with glacial acetic acid.

In the case of sensitive substituents, the nitration can also be carried out in a mixture of acetic acid or trifluoroacetic acid with sodium nitrate. To this end, the pyridine derivative is suspended together with sodium nitrate in acetic or trifluoroacetic acid and the reaction is then carried out.

The nitration is particularly preferably made anhydrous in the presence of acetic acid. In this process, the nitric acid is added to the pyridine derivative Ib dissolved or suspended in acetic anhydride and the mixture is stirred until the reaction has ended. Expediently, both reaction components, pyridine derivative Ib and nitric acid, can be diluted with glacial acetic acid.

At temperatures above 20° C, acetyl nitrate is formed from mixtures of nitric acid and acetic anhydride.

Instead of acetic anhydride as a solvent, trifluoroacetic anhydride can also be used. Indifferent solvents which are not attacked by nitric acid under the particular conditions of the nitration can likewise be used. Aliphatic chlorohydrocarbons such as dichloromethane, chloroform, tetrachloromethane, 1,2-dichloroethane and polychloroethanes are preferred. Also suitable, however, are gasoline fractions, naphtha, nitromethane, acetonitrile, ethanol, ether, acetone, mono- and dichlorobenzenes and also nitrobenzenes.

The reaction is in general carried out at from −20 to 400° C., preferably from 0 to 200° C., particularly preferably from 20 to 120° C.

The molar ratios in which the starting compounds required are reacted with one another are from 0.9:1 to 3.0:1, preferably from 1.1:1 to 1.5:1 for the ratio of nitric acid to pyridine derivative Ib. The concentration of the starting materials in the solvent is from 0.1 to 5 mol/l, preferably from 0.3 to 2 mol/l.

If the reaction is exothermic, a temperature of from 20 to 40° C. is expediently maintained by cooling during the addition of the first half of the nitric acid and the cold bath can then be removed with increasingly gentler course of the reaction. If the extent of reaction is unsatisfactory, it may be necessary to carry the reaction to completion by heating, eg. to 120° C. The reaction time is a quarter of an hour to 24 hours, depending on the given temperature.

Working up can be carried out in a customary manner, eg. by filtration, washing the solid material, distillation of filtrate and wash filtration. Advantageously, the pyridine derivatives Ia can be precipitated in water or ice-water, filtered off with suction, freed from acid residues using aqueous alkaline solutions and worked up as described.

The process for preparing the compounds IIa, where at least one of the radicals $R^2$ to $R^4$ of the abovementioned meanings is nitro, consists in reacting a pyridinecarboxylic anhydride or its N-oxide IIb with nitrating agents and is carried out in the same manner as the reaction of the pyridine derivatives Ib described above.

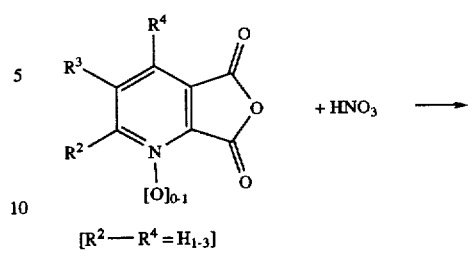

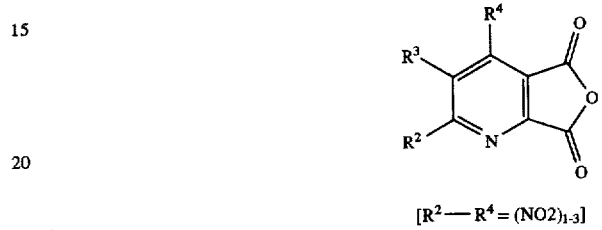

Instead of at the stage of the pyridinedicarboxylic anhydrides or their N-oxides IIb, the nitration can also be carried out at the corresponding diester or N-oxide stage thereof Vb. These can then be converted either by hydrolysis to the carboxylic acid salts and cyclization to the anhydrides IIa or reacted directly with the amine III to give carboxylic ester hemiamides VI, which, after hydrolysis to IV, can be cyclized to give the compounds Ia according to the invention.

The removal of the pyridine-N-oxide oxygen can even be carried out under the conditions of the nitration in acetic anhydride as a reaction medium, otherwise it can be removed according to the literature conditions (Houben-Weyl, Methoden der org. Chemie [Methods of Organic Chemistry], G. Thieme Verlag, Stuttgart, Vol. 10/2 p. 714 (4th edition)) by passing in nitrogen monoxide or by heating at 70 to 80° C. for one hour with phosphorus(III) chloride. A general survey of the preparation of pyridine-N-oxides is also taken from the same place.

The abovementioned process for preparing pyridinecarboxylic acid esters of the formulae Va–c

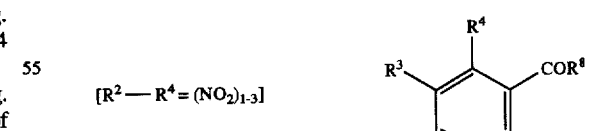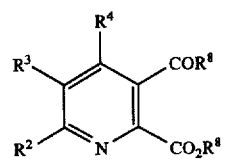

where $R^2$ to $R^4$ have the abovementioned meanings, at least one of the radicals being nitro and $R^5$ being any desired substituted alkyl radical, consists in the treatment of a pyridinedicarboxylic acid ester or its N-oxide of the formulae Va'–Vc'

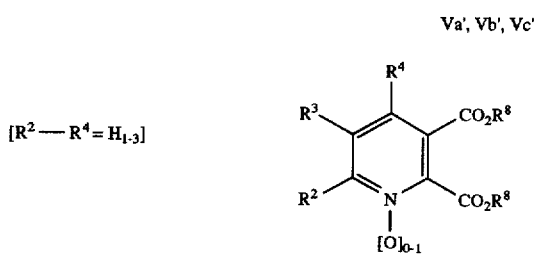

Va', Vb', Vc'

[R² — R⁴ = H₁₋₃]

where R² to R⁸ have the abovementioned meanings, at least one of the radicals R² to R⁴ (namely that (those) which is (are)- replaced by nitro) being hydrogen, with nitrating agents and, if approprite, deoxygenation.

The process is carried out in the same manner as the reaction of the pyridine derivatives Ib described above.

The abovementioned conversions then follow to give the pyridine derivatives Ia.

In comparison with the prior art, the novel nitro-substituted pyridine-2,3-dicarboxylic anhydrides, esters and imides are accessible in high yields in a particularly simple manner. Nitro-substituted pyridine-2,3-dicarboxylic anhydrides and imides were previously unknown.

In the diester series, the 6-methyl-5-nitro, the 6-chloro-5-nitro and the 6-amino-5-nitro derivative are known.

They all have to be synthesized in an involved reaction based on ethoxymethyleneoxalacetic ester and a nitroketone component. In the case of nitroacetone the yield is only 18% (EP-A 227 932); moreover, nitroacetone cannot be stored and can spontaneously de40 compose (Beilstein III, 661).

In the case of the nitration of 5-chloro-6-hydroxynicotinic acid, the carboxylic acid radical is removed and replaced by a nitro group (EP-A-467 308).

Against the background of the teaching found from the prior art, the nitrations according to the invention were therefore not to be expected. It is also surprising that when using the unsubstituted N-oxides nitration does not take place in the 4-position, but in the 5-position. According to Houben-Weyl, Methoden der org. Chemie [Methods of Organic Chemistry], G. Thieme Verlag Stuttgart, Vol. 10/1 p. 713 (4th edition), a substitution in the 4- or 6-position would have been expected here.

In the context of the preparation of the compounds according to the invention, it has furthermore been found

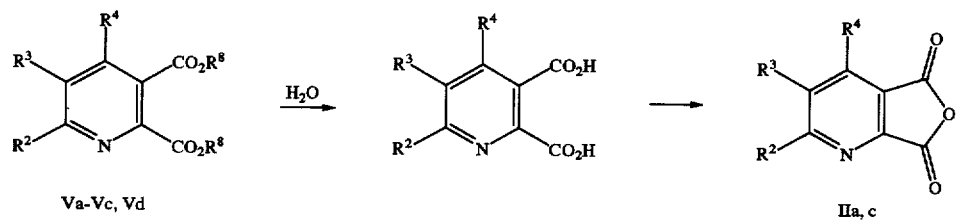

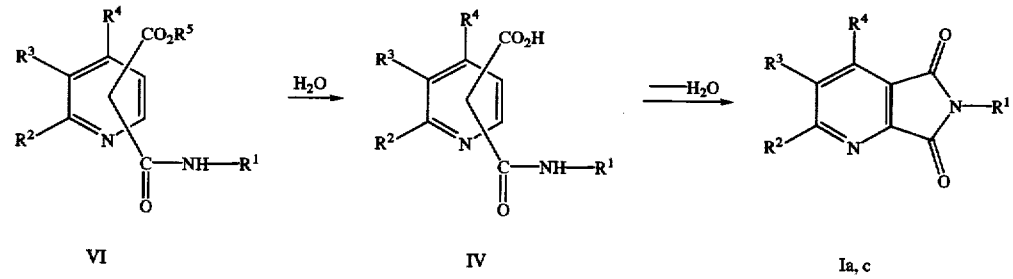

that amino-substituted pyridine derivatives of the formula Ic

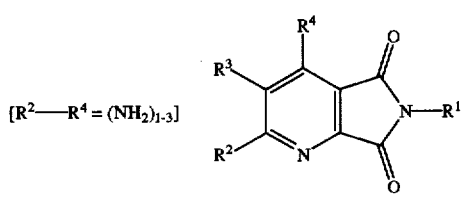

where $R^2$ to $R^4$ have the abovementioned meanings, at least one of the radicals being amino, are obtained when pyridine derivatives of the formula Ia are subjected to reduction.

It has furthermore been found that pyridine derivatives of the fomula IIc

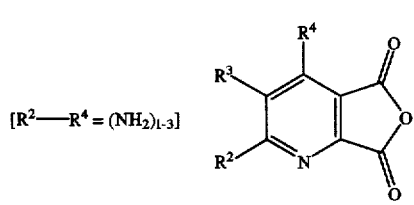

where $R^2$ to $R^4$ have the abovementioned meanings, at least one of the radicals being amino, are obtained when pyridine derivatives of the formula IIa are subjected to reduction.

Instead of at the stage of the pyridinedicarboxylic anhydrides IIa, the reduction can also be carried out at the corresponding diester stage Va–Vc. These can then be converted to the anhydrides IIc by hydrolysis to the carboxylic acid salts and cyclization (if appropriate using an amine protective group) or reacted directly with the amine III to give carboxylic ester hemiamides VI which, after hydrolysis to IV, can be cyclized to give the compounds Ic according to the invention (if appropriate using an amine protective group).

A process for preparing compounds Ic, where at least one of the radicals $R^2$ to $R^4$ is amino, consists in the reduction of a pyridine derivative Ia.

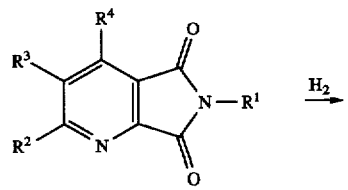

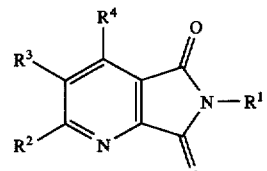

The reduction can be carried out catalytically on all customary catalysts with or without pressure in a continuous or discontinuous manner using hydrogen or hydrazine hydrate as the hydrogen source. Suitable catalysts are, for example, Pt, Pd, Re, Ni, Pd and Ru or mixtures, eg. Ra/Ni, Pt/Ru oxides. Other catalysts are mentioned in Houben-Weyl, Methoden der org. Chemie. [Methods of Organic Chemistry], G. Thieme Verlag, Stuttgart, Vol. 4/1c pp. 506–537 (4th edition), as well as promoters and accelerators for accelerating the hydrogenation. Reaction conditions, choice of the solvent, transfer conditions, details of selective hydrogenation in the presence of, for example, halogens and details of working up are found in the same place, and also in Vol. 11/1 pp. 360–381. The latter also describes the reduction with iron (p. 394) with hydrogen sulfide, sulfides and polysulfides (p. 409), and also tin and tin(II) chloride (p. 422), sodium dithionite (p. 437), iron(II) hydroxide (p. 443), lithium aluminum hydride (p. 447), sulfites (p. 457), zinc (p. 463), aluminum (p. 469) or an electrolytic reduction.

A process for preparing pyridine derivatives of the formula IIc where at least one of the radicals $R^2$ to $R^4$ from the abovementioned meanings is amino, consists in the reduction of a pyridine derivative IIa.

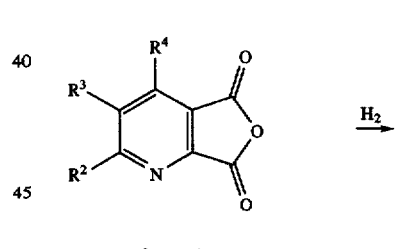

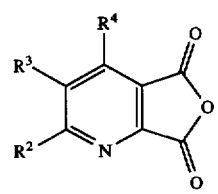

The reduction is carried out in the same manner as the reduction of the pyridine derivatives Ia described above.

A process for preparing pyridine derivatives of the formula Vd where at least one of the radicals $R^2$ to $R^4$ from the abovementioned meanings is amino, consists in the reduction of a pyridine derivative Va–Vc.

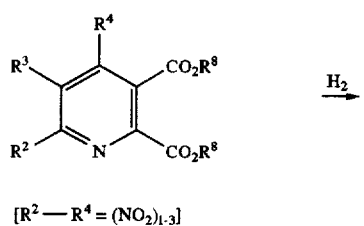

$[R^2 — R^4 = (NO_2)_{1-3}]$ $\xrightarrow{H_2}$

Va-c

Vd

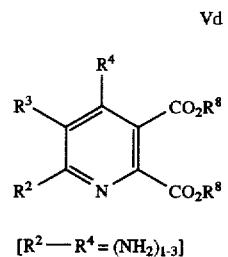

$[R^2 — R^4 = (NH_2)_{1-3}]$

The reduction is carried out in the same manner as the reduction of the pyridine derivatives Ia described above.

A further process for preparing pyridine derivatives of the formula Ve where at least one of the radicals $R^2$ to $R^4$ is $NR^{6'}R^{7'}$, $R^{6'}$ and $R^{7'}$ independently of one another being hydrogen or $C_1$–$C_4$-alkyl, and $R^{6'}$ additionally being benzyl or $C_1$–$C_4$-alkoxy, consists in the reaction of a pyridine derivative Vf with an amine.

Vf

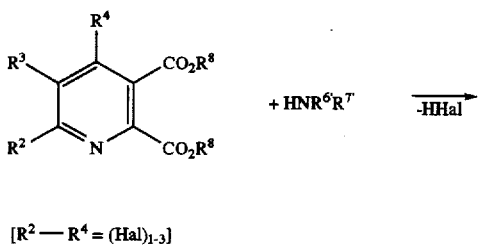

$[R^2 — R^4 = (Hal)_{1-3}]$ $+ HNR^6R^{7'} \xrightarrow{-HHal}$

Ve

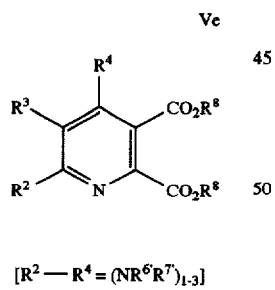

$[R^2 — R^4 = (NR^6R^{7'})_{1-3}]$

For this purpose, the pyridine derivative Vf is initially introduced in one of the abovementioned inert solvents and the amine, as a gas or liquid, and an auxiliary base are added.

In general, the reaction is carried out at from –20 to 250° C., preferably from 0 to 200° C., particularly preferably from 20 to 180° C.

The molar ratios in which the starting compounds required are reacted with one another are from 0.9:1 to 3.0:1, preferably from 1.1:1 to 1.5:1, for the ratio of amine to pyridine derivative Vf. The concentration of the starting materials in the solvent is from 0.1 to 5 mol/l, preferably from 0.3 to 2 mol/l.

If only approximately stoichiometric amounts of the amine are employed, expediently from 0.9 to 1.1 equivalents of an organic auxiliary base, based on the starting substance Vf, must be added. Suitable auxiliary bases are organic bases such as trimethylamine, triethylamine, N-ethyldiisopropylamine, triisopropylamine, N,N-dimethylaniline, N,N-dimethylcyclohexylamine, N-methylpyrrolidone, pyridine, quinoline, α,β,γ-picoline, 2,4- and 2,6-lutidine and triethylenediamine.

In the context of the preparation of the compounds according to the invention, it has furthermore been found that amino-substituted pyridine derivatives of the formula Ic Ic

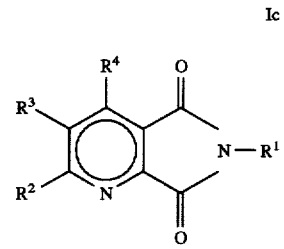

$[R^2 — R^4 = (NH_2)_{1-3}]$ where $R^2$ to $R^4$ have the abovementioned meaning, at least one of the radicals being amino, are obtained when pyridine derivatives of the formula Id where $R^2$ to $R^4$ have the abovementioned meanings, at least one of the radicals being halogen, are reacted with a metal cyanate and the isocyanate formed is hydrolyzed in situ.

Id

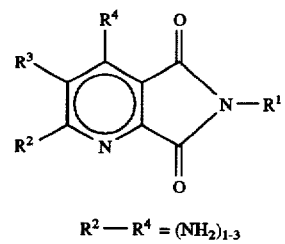

$R^2 — R^4 = Hal_{1-3}$ $\xrightarrow{\text{MeOCN} \quad H_2O}$

Ic $R^2 — R^4 = (NH_2)_{1-3}$

For this purpose, the pyridine derivative Id is initially introduced in one of the abovementioned solvents, expediently with addition of at least 1 to 6 equivalents, preferably 2 to 3 equivalents, of water, the metal cyanate is added and the reaction is then carried out.

In general, the reaction is carried out at from 20 to 200° C., preferably from 80 to 150° C., particularly preferably from 100 to 130° C.

The molar ratios in which the pyridine derivative Id and the metal cyanate are reacted with one another are from 1:0.9 to 1:3, preferably from 1:1.5 to 1:2.5. The concentration of the starting materials in the solvent is from 0.1 to 5 mol/l, preferably from 0.3 to 2 mol/l.

Suitable cyanates are the salts derived from alkali metals and alkaline earth metals and also iron, cobalt, nickel, copper and zinc, and also ammonium cyanate.

For working up, the reaction mixture is extracted with water to remove the salts and dried, and the organic phase is purified, eg. by chromatography or distillation. The reaction products, however, are usually sufficiently pure, so that it is only necessary to filter off from the precipitated salt and to concentrate the organic phase.

In comparison to the prior art, the novel amino-substituted pyridine-2,3-dicarboxylic anhydrides, esters and imides are accessible in high yields in a particularly simple manner. Amino-substituted pyridine-2,3-dicarboxylic anhydrides were hitherto unknown. In the imide series, 6-amino-5-cyano-4-phenylpyridine-2,3-dicarboxyimide was accessed via a photooxygenation and ring closure reaction (synth. Commun. 22, 2053). Of the esters, dimethyl 4-aminopyridine-2,3-dicarboxylate was known by esterification of the corresponding acid, which was isolated from a poisonous fungus [CA. 111, 112 292]. Diethyl 5,6-diaminopyridine-2,3-dicarboxylate was prepared by reduction of an analogous 5-nitro ester, this being carried out with an excess of 261 mol % of palladium in the presence of hydrogen (EP-A 227 932). Diethyl 6-amino-5-nitropyridine-2,3-dicarboxylate was obtained by nucleophilic displacement of a corresponding 6-chloro derivative with ammonia, no details of the yield being given (EP-A 227 932). Dimethyl and diethyl 5-amino-6-methylpyridine-2,3-dicarboxylates were obtained in an involved manner by esterification and Hofmann degradation of a poorly accessible pyridinetricarboxamide derivative (Beilstein 4-22-006875).

All processes are complicated multistage reactions or require uneconomical amounts of catalyst.

With respect to the intended use of the compounds I, examples of suitable substituents are the following radicals:

$R^1$ hydrogen;

$C_1$–$C_4$-alkoxy such as methoxy, ethoxy, propoxy, 1-methylethoxy, butoxy, 1-methylpropoxy, 2-methylpropoxy and 1,1-dimethylethoxy, in particular methoxy, ethoxy, 1-methylethoxy and 1,1-dimethylethoxy;

$C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, in particular propyl, 1-methylethyl and 1,1-dimethylethyl, the radicals mentioned being able to carry one to three of the following groups:

$C_1$–$C_4$-alkoxy as mentioned above, in particular methoxy and ethoxy;

$C_1$–$C_4$-haloalkoxy such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, in particular trifluoromethoxy and pentafluoroethoxy;

$C_1$–$C_4$-alkylthio such as methylthio, ethylthio, propylthio, 1-methylethylthio, n-butylthio, propylthio, 1-methylethylthio, 1-methylpropylthio, 2-methylpropylthio and 1,1-dimethylethylthio, in particular methylthio and ethylthio;

$C_1$–$C_4$-haloalkylthio such as difluoromethylthio, trifluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio and pentafluoroethylthio, in particular trifluoromethylthio and pentafluoroethylthio;

($C_1$–$C_4$-dialkyl)amino such as dimethylamino, diethylamino, dipropylamino, diisopropylamino, dibutylamino, methylethylamino, in particular dimethylamino and methylethylamino;

$C_3$–$C_8$-cycloalkyl such as cyclopropyl, cyclobutyl, cyclopentyl, cyclohexyl, cycloheptyl and cyclooctyl, in particular cyclopropyl, cyclopentyl and cyclohexyl;

halogen such as fluorine, chlorine, bromine, iodine, in particular fluorine and chlorine;

additionally $C_3$–$C_8$-cycloalkyl as mentioned above, in particular cyclopropyl, cyclobutyl, cyclopentyl and cyclohexyl, which can carry one to three of the following groups: $C_1$–$C_6$-alkyl as mentioned above, in particular methyl, ethyl and isopropyl; haloalkyl as mentioned above for the homologous haloalkylthio radicals, in particular trifluoromethyl; $C_1$–$C_4$-alkoxy as mentioned above, in particular methoxy and ethoxy; $C_1$–$C_4$-haloalkoxy as mentioned above, in particular trifluoromethoxy; halogen as mentioned above, in particular fluorine and chlorine;

$C_3$–$C_6$-alkenyl such as 2-propenyl, 2-methylethenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 1-, 2-, 3-, 4- or 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-pentenyl and ethyl-2-methyl-2-pentenyl, in particular ethenyl, 2-propenyl, 1-methylethenyl, 2-butenyl, 3-butenyl, 1-methylpropyl, 1-methyl-2-propenyl, 2-methyl-2-propenyl, which can be mono- to trisubstituted by halogen, in particular fluorine and chlorine;

additionally $C_3$–$C_6$-alkynyl such as propargyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 3-methyl-1-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-4-pentynyl, 4-methyl-2-pentynyl, 1,1- dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, in particular 1-methyl-2-propynyl and 1,1-dimethyl-2-propynyl, which can be mono- to trisubstituted by halogen as mentioned above, in particular fluorine and chlorine, and/or monosubstituted by phenyl;

$R^2$, $R^3$ and $R^4$ at least one of the radicals is nitro, an $OR^5$ or $NR^6R^7$ group and the other radicals are:

hydrogen, halogen as mentioned under $R^1$, in particular fluorine and chlorine; cyano; $C_1$–$C_6$-alkyl as mentioned under $R^1$, in particular methyl, ethyl, propyl, 1-methylethyl and 1,1-dimethylethyl, which can carry one to five halogen atoms, as mentioned under $R^1$, in particular fluorine and chlorine, and/or one or two of the following radicals: $C_1$–$C_4$-alkoxy as mentioned under $R^1$, in particular methoxy, ethoxy, 1-methylethoxy and 1,1-dimethylethoxy; $C_1$–$C_4$-haloalkoxy as mentioned under $R^1$, in particular halomethoxy such as difluoromethoxy and trifluoromethoxy; $C_1$–$C_4$-alkylthio as mentioned under $R^1$, in particular methylthio and ethylthio; $C_1$–$C_4$-haloalkylthio, as mentioned under $R^1$, in particular difluoromethylthio and trifluoromethylthio;

$C_3$–$C_6$-cycloalkyl as mentioned under $R^1$, in particular cyclopropyl;

additionally benzyl, which can be mono- to trisubstituted by $C_1$–$C_4$-alkyl as mentioned under $R^1$, in particular methyl, ethyl and 1-methylethyl; $C_1$–$C_4$-haloalkyl as mentioned under $R^1$, in particular trifluoromethyl and chlorodifluoromethyl; $C_1$–$C_4$-alkoxy as mentioned under $R^1$, in particular methoxy and ethoxy; $C_1$–$C_4$-haloalkoxy as mentioned under $R^1$, in particular trifluoromethoxy, trichloromethoxy and pentafluoroethoxy; $C_1$–$C_4$-alkylthio as mentioned under $R^1$, in particular methylthio and ethylthio; $C_1$–$C_4$-haloalkylthio as mentioned under $R^1$, in particular difluoromethylthio, trifluoromethylthio and pentafluoromethylthio; halogen, in particular fluorine and chlorine; cyano or nitro;

additionally $C_3$–$C_8$-cycloalkyl, as mentioned under $R^1$, in particular cyclopropyl, cyclopentyl and cyclohexyl; which can be mono- to trisubstituted by $C_1$–$C_4$-alkyl as mentioned under $R^1$, in particular methyl and ethyl; or halogen as mentioned under $R^1$, in particular fluorine and chlorine;

$C_2$–$C_6$-alkenyl as mentioned under $R^1$, additionally 1-ethenyl, 1-propenyl, 1-methyl-1-propenyl, 2-methyl-1-propenyl, 1-pentenyl, 1-methyl-1-butenyl, 2-methyl-1-butenyl, 1-ethyl-1-propenyl, 1-methyl-1-pentenyl, $^2$-methyl-1-pentenyl, $^3$-methyl-1-pentenyl, 4-methyl-1-pentenyl, 1,2-dimethyl-1-butenyl, 1,3-dimethyl-1-butenyl, 2,3-dimethyl-1-butenyl, 3,3-dimethyl-1-butenyl, ethyl-1-butenyl, $^2$-ethyl-1-butenyl, 1-ethyl-2-methyl-1-pentenyl, in particular ethenyl, 1-propenyl, 2-propenyl, 1-methylethenyl, 1-butenyl, 2-butenyl, 3-butenyl, 1-methylpropenyl, 1-methyl-2-propenyl, 2-methyl-1-propenyl, 2-methyl-2-propenyl, which can be mono- to trisubstituted by halogen as mentioned under $R^1$, in particular fluorine and chlorine; or $C_1$–$C_3$-alkoxy as mentioned under $R^1$, in particular methoxy and ethoxy; and/or monosubstituted by phenyl, the phenyl radical in turn being able to carry one to three of the following groups: alkyl as mentioned under $R^1$, in particular methyl, ethyl and 1-methylethyl; haloalkyl as mentioned under $R^1$, in particular trifluoromethyl and chlorodifluoromethyl; alkoxy as mentioned under $R^1$, in particular methoxy and ethoxy; haloalkoxy as mentioned under $R^1$, in particular trifluoromethoxy, trichloromethoxy and pentafluoroethoxy; alkylthio as mentioned under $R^1$, in particular methylthio and ethylthio; haloalkylthio as mentioned under $R^1$, in particular difluoromethylthio, trifluoromethylthio and pentafluoromethylthio; halogen as mentioned under $R^1$, in particular fluorine and chlorine; cyano or nitro;

$C_2$–$C_6$-alkynyl, as mentioned under $R^1$, in addition ethynyl, 1-propynyl, 1-butynyl, 1-pentynyl, 1-hexynyl, 3-methyl-1-pentynyl, 4-methyl-1-pentynyl, in particular ethynyl, 1-propynyl and propargyl, which can be mono- to trisubstituted by halogen as mentioned above, in particular fluorine and chlorine; or alkoxy as mentioned above, in particular methoxy and ethoxy; and/or monosubstituted by phenyl, the phenyl radical in turn being able to carry one to three of the following groups: alkyl as mentioned above, in particular methyl, ethyl and 1-methylethyl; haloalkyl as mentioned above, in particular trifluoromethyl and chlorodifluoromethyl; alkoxy as mentioned above, in particular methoxy and ethoxy; haloalkoxy as mentioned above, in particular trifluoromethoxy, trichloromethoxy and pentafluoroethoxy; alkylthio as mentioned above, in particular methylthio and ethylthio-; haloalkylthio as mentioned above, in particular difluoromethylthio, trifluoromethylthio and pentafluoromethylthio; halogen as mentioned above, in particular fluorine and chlorine; cyano or nitro;

additionally $C_1$–$C_4$-alkoxy or -alkylthio as mentioned under $R^1$, in particular methoxy and ethoxy, methylthio and ethylthio;

$C_1$–$C_4$-haloalkoxy or -haloalkylthio as mentioned above, in particular trifluoromethoxy, trichloromethoxy and pentafluoroethoxy, difluoromethylthio, trifluoromethylthio and pentafluoroethylthio;

$C_2$–$C_5$-alkenyloxy such as vinyloxy, 2-propenyloxy, 1-methylethenyloxy, 2-methyl-3-butenyloxy, in particular 2-propenyloxy and 2-methyl-3-butenyloxy;

$C_2$–$C_5$-alkynyloxy such as ethynyloxy, 2-propynyloxy, 1-methylethynyloxy, 2-methyl-3-butynyloxy, in particular 2-propynyloxy and 2-methyl-3-butynyloxy;

$C_1$–$C_4$-alkylsulfinyl such as methylsulfinyl, ethylsulfinyl, n-propylsulfinyl, i-propylsulfinyl, n-butylsulfinyl, tert-butylsulfinyl, in particular methylsulfinyl;

$C_1$–$C_4$-alkylsulfonyl such as methylsulfonyl, ethylsulfonyl, n-propylsulfonyl, i-propylsulfonyl, n-butylsulfonyl, tert-butylsulfonyl, in particular methylsulfonyl;

$C_1$–$C_4$-haloalkylsulfonyl such as trifluoromethylsulfonyl, pentafluoroethylsulfonyl, monofluorobutylsulfonyl, in particular trifluoromethylsulfonyl;

phenoxy or phenylthio, which can be mono- to trisubstituted by $C_1$–$C_4$-alkyl as mentioned under $R^1$, in particular methyl, ethyl and isopropyl; haloalkyl as mentioned under $R^1$, in particular trifluoromethyl and chlorodifluoromethyl; alkoxy as mentioned above, in particular trifluoromethoxy, trichloromethoxy and pentafluoroethoxy; alkylthio as mentioned above, in particular methylthio and ethylthio;

haloalkylthio as mentioned above, in particular difluoromethylthio, trifluoromethylthio and pentafluoromethylthio; halogen as mentioned above, in particular fluorine and chlorine; cyano or nitro;

a 5- or 6-membered saturated or aromatic heterocyclic radical, containing one or two heteroatoms selected from the group consisting of oxygen, sulfur and nitrogen, such as tetrahydrofuryl, tetrahydropyranyl, furyl, thienyl, thiazolyl, pyrazolyl, pyrrolyl, pyridyl, morpholino, piperidino, pyrimidyl, for example 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furyl, 3-furyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrazolyl, 4-pyrazolyl, 5-pyrazolyl, 2-pyridyl, 3-pyridyl and 4-pyridyl, which can carry one to three of the following substituents: $C_1$–$C_3$-alkyl as mentioned above, in particular methyl and ethyl, halogen as mentioned above, in particular fluorine and chlorine, $C_1$–$C_3$-alkoxy as mentioned under $R^1$, in particular methoxy and ethoxy; or $C_1$–$C_4$-alkoxycarbonyl such as methoxycarbonyl and ethoxycarbonyl, in particular methoxycarbonyl;

phenyl, which can carry one to three of the following groups:

$C_1$–$C_6$-alkyl as mentioned under $R^1$, in particular methyl, ethyl and isopropyl; $C_1$–$C_6$-haloalkyl as mentioned under $R^1$, in particular trifluoromethyl and chlorodifluoromethyl; $C_1$–$C_6$-alkoxy as mentioned under $R^1$, in particular methoxy and ethoxy; $C_1$–$C_6$-haloalkoxy as mentioned under $R^1$, in particular trifluoromethoxy, trichalomethoxy and pentafluoroethoxy; $C_1$–$C_6$-alkylthio as mentioned under $R^1$, in particular methylthio and ethylthio; $C_1$–$C_6$haloalkylthio as mentioned under $R^1$, in particular difluoromethylthio, trifluoromethylthio and pentafluoromethylthio; halogen as mentioned under $R^1$, in particular fluorine and chlorine; cyano or nitro;

$R^5$ hydrogen, $C_1$–$C_4$-alkylcarbonyl, $C_1$–$C_4$-haloalkylcarbonyl, $C_1$–$C_4$-alkoxycarbonyl, $C_1$–$C_4$-alkoxy-$C_2$–$C_4$-alkoxycarbonyl, $C_1$–$C_4$-alkylcarbamoyl, $C_1$–$C_4$-dialkylcarbamoyl, $C_1$–$C_4$-alkylsulfonyl, $C_1$–$C_4$-haloalkylsulfonyl, sulfamoyl, $C_1$–$C_4$-alkylaminosulfonyl, $C_1$–$C_4$-dialkylaminosulfonyl, phenylsulfonyl, which can be mono- to trisubstituted by $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, halogen, cyano or nitro, the alkyl, alkyloxy, haloalkyl, alkylthio and alkylamino constituents in the individual radicals contained in the definitions corresponding to those indicated above in the individual definitions listed;

$R^6$ hydrogen, $C_1$–$C_4$-alkyl, in particular methyl and ethyl, benzyl, $C_1$–$C_4$-alkoxy, eg. methoxy and ethoxy, or together with $R^7$ C=S;

$R^7$ $C_1$–$C_4$-alkyl, in particular methyl and ethyl, and the radicals listed for $R^5$.

Examples of preferred radical combinations in the pyridine ring can be taken from the table below, $R^1$ corresponding to a radical from the group L1 to L66, in particular to a 1-(cyclopropyl)ethyl radical or a cyclopropyl radical.

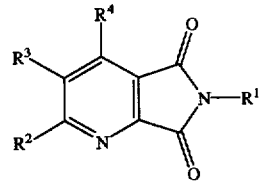

I

| $R^2$ | $R^3$ | $R^4$ |
|---|---|---|
| $NO_2$ | H | H |
| $NO_2$ | F | H |
| $NO_2$ | H | F |
| $NO_2$ | F | F |
| $NO_2$ | Cl | H |
| $NO_2$ | H | Cl |
| $NO_2$ | Cl | Cl |
| $NO_2$ | F | Cl |
| $NO_2$ | Cl | F |
| $NO_2$ | CN | H |
| $NO_2$ | H | CN |
| $NO_2$ | CN | CN |
| $NO_2$ | CN | F |
| $NO_2$ | F | CN |
| $NO_2$ | Cl | CN |
| $NO_2$ | CN | Cl |
| $NO_2$ | $CH_3$ | H |
| $NO_2$ | H | $CH_3$ |
| $NO_2$ | $CH_3$ | $CH_3$ |
| $NO_2$ | F | $CH_3$ |
| $NO_2$ | $CH_3$ | F |
| $NO_2$ | $CH_3$ | Cl |
| $NO_2$ | Cl | $CH_3$ |
| $NO_2$ | $C_2H_5$ | F |
| $NO_2$ | F | $C_2H_5$ |
| $NO_2$ | $CF_3$ | H |
| $NO_2$ | H | $CF_3$ |
| $NO_2$ | Cl | $CF_3$ |
| $NO_2$ | $CF_3$ | Cl |
| $NO_2$ | $C_2F_5$ | H |
| $NO_2$ | H | $C_2F_5$ |
| $NO_2$ | $CH_2OCH_3$ | H |
| $NO_2$ | H | $CH_2OCH_3$ |
| $NO_2$ | $CH_2OCH_3$ | F |
| $NO_2$ | $CH_2SCH_3$ | H |
| $NO_2$ | H | $CH_2SCH_3$ |
| $NO_2$ | $CH_2SCH_3$ | Cl |
| $NO_2$ | Cl | $CH_2SCH_3$ |
| $NO_2$ | $CH_2$-cyclopropyl | H |
| $NO_2$ | 1-(cyclopropyl)ethyl | H |
| $NO_2$ | $CH_2CN$ | H |
| $NO_2$ | H | $CH_2CN$ |
| $NO_2$ | $CH_3$ | $CH_2CN$ |
| $NO_2$ | benzyl | H |
| $NO_2$ | Cl | benzyl |
| $NO_2$ | benzyl | F |
| $NO_2$ | F | benzyl |
| $NO_2$ | 4-chlorobenzyl | H |
| $NO_2$ | 3-$CF_3$-benzyl | H |
| $NO_2$ | 2,4-$Cl_2$-benzyl | H |
| $NO_2$ | 3-$OCH_3$-phenyl | H |
| $NO_2$ | H | 3-$OCH_3$-benzyl |
| $NO_2$ | 3-CN-benzyl | H |
| $NO_2$ | cyclopropyl | H |
| $NO_2$ | cyclopropyl | Cl |
| $NO_2$ | cyclopropyl | F |
| $NO_2$ | CH=$CH_2$ | H |
| $NO_2$ | F | CH=$CH_2$ |
| $NO_2$ | CF=$CF_2$ | H |
| $NO_2$ | $CH_3$ | CF=$CF_2$ |
| $NO_2$ | $CH_3$ | benzyl |
| $NO_2$ | CH=CH—$OCH_3$ | H |

-continued

| R² | R³ | R⁴ |
|---|---|---|
| NO₂ | CH=CH—OCH₃ | Cl |
| NO₂ | CH=CH—OCH₃ | F |
| NO₂ | CH=CH-phenyl | H |
| NO₂ | CH=CH-phenyl | F |
| NO₂ | CH=CH-phenyl | Cl |
| NO₂ | CH=CH-(3-chlorophenyl) | H |
| NO₂ | CH=CH-(3-chlorophenyl) | F |
| NO₂ | C≡CH | H |
| NO₂ | CH₂—C≡CH | H |
| NO₂ | CH₂—C≡CH | F |
| NO₂ | CH₃O | H |
| NO₂ | CH₃O | F |
| NO₂ | CH₃O | Cl |
| NO₂ | CH₃O | CH₃ |
| NO₂ | H | CH₃O |
| NO₂ | Cl | CH₃O |
| NO₂ | F | CH₃O |
| NO₂ | CH₃ | CH₃O |
| NO₂ | CH₃O | CH₃O |
| NO₂ | CH₃S | H |
| NO₂ | CH₃S | F |
| NO₂ | CH₃S | Cl |
| NO₂ | CH₃S | CH₃ |
| NO₂ | H | CH₃S |
| NO₂ | F | CH₃S |
| NO₂ | Cl | CH₃S |
| NO₂ | CH₃ | CH₃S |
| NO₂ | CF₃O | H |
| NO₂ | CF₃O | F |
| NO₂ | CF₃O | Cl |
| NO₂ | F₂CHO | H |
| NO₂ | F₂CHO | F |
| NO₂ | F₂CHO | Cl |
| NO₂ | SCF₃ | H |
| NO₂ | SCF₃ | F |
| NO₂ | SCF₃ | Cl |
| NO₂ | CH₃SO | H |
| NO₂ | CH₃SO | F |
| NO₂ | CH₃SO | Cl |
| NO₂ | CH₃SO₂ | H |
| NO₂ | CH₃SO₂ | Cl |
| NO₂ | CH₃SO₂ | F |
| NO₂ | CF₃SO₂ | H |
| NO₂ | CF₃SO₂ | F |
| NO₂ | CF₃SO₂ | Cl |
| NO₂ | O-phenyl | H |
| NO₂ | O-phenyl | F |
| NO₂ | O-(4-Cl-phenyl) | H |
| NO₂ | O-(3-CF₃-phenyl) | H |
| NO₂ | O-(2,4-Cl₂-phenyl) | H |
| NO₂ | O-(4-CH₃O-phenyl) | H |
| NO₂ | O-(3-CN-phenyl) | H |
| NO₂ | S-phenyl | H |
| NO₂ | S-(3-Cl-phenyl) | H |
| NO₂ | 2-tetrahydrofuranyl | H |
| NO₂ | 3-tetrahydrofuranyl | H |
| NO₂ | 2-tetrahydrothienyl | H |
| NO₂ | 3-tetrahydrothienyl | H |
| NO₂ | 2-tetrahydropyranyl | H |
| NO₂ | 3-tetrahydropyranyl | H |
| NO₂ | 4-tetrahydropyranyl | H |
| NO₂ | 2-furyl | H |
| NO₂ | 3-furyl | H |
| NO₂ | 2-thienyl | H |
| NO₂ | 3-thienyl | H |
| NO₂ | 3-isoxazolyl | H |
| NO₂ | 4-isoxazolyl | H |
| NO₂ | 5-isoxazolyl | H |
| NO₂ | 3-isothiazolyl | H |
| NO₂ | 4-isothiazolyl | H |
| NO₂ | 5-isothiazolyl | H |
| NO₂ | 2-oxazolyl | H |
| NO₂ | 4-oxazolyl | H |
| NO₂ | 5-oxazolyl | H |
| NO₂ | 2-thiazolyl | H |
| NO₂ | 4-thiazolyl | H |

-continued

| R² | R³ | R⁴ |
|---|---|---|
| NO₂ | 5-thiazolyl | H |
| NO₂ | 2-imidazolyl | H |
| NO₂ | 4-imidazolyl | H |
| NO₂ | 5-imidazolyl | H |
| NO₂ | 2-pyrrolyl | H |
| NO₂ | 3-pyrrolyl | H |
| NO₂ | 3-pyrazolyl | H |
| NO₂ | 4-pyrazolyl | H |
| NO₂ | 5-pyrazolyl | H |
| NO₂ | 2-pyridyl | H |
| NO₂ | 3-pyridyl | H |
| NO₂ | 4-pyridyl | H |
| NO₂ | phenyl | H |
| NO₂ | 4-Cl-phenyl | H |
| NO₂ | 2,4-Cl₂-phenyl | H |
| NO₂ | 3-CF₃-phenyl | H |
| NO₂ | 3-CH₃O-phenyl | H |
| H | NO₂ | H |
| H | NO₂ | F |
| H | NO₂ | Cl |
| H | NO₂ | CN |
| H | NO₂ | CH₃ |
| H | NO₂ | CH₃O |
| H | NO₂ | C₂H₅O |
| H | NO₂ | CH₃S |
| H | NO₂ | C₂H₅S |
| H | NO₂ | benzyl |
| H | NO₂ | CF=CF₂ |
| H | NO₂ | C₂F₅ |
| H | NO₂ | cyclopropyl |
| H | NO₂ | C₂H₅ |
| H | NO₂ | CF₃O |
| H | NO₂ | F₂CHO |
| H | NO₂ | C₂F₅O |
| H | NO₂ | CF₃S |
| H | NO₂ | F₂CHS |
| H | NO₂ | CF₃ |
| H | NO₂ | CH₃SO |
| H | NO₂ | CH₃SO₂ |
| H | NO₂ | CF₃SO₂ |
| H | NO₂ | O-phenyl |
| H | NO₂ | O-(4-Cl-phenyl) |
| H | NH₂ | O-(3-CF₃-phenyl) |
| H | NH₂ | H |
| H | NH₂ | F |
| H | NH₂ | Cl |
| H | NH₂ | CN |
| H | NH₂ | CH₃ |
| H | NH₂ | CH₃O |
| H | NH₂ | C₂H₅O |
| H | NH₂ | CH₃S |
| H | NH₂ | C₂H₅S |
| H | NH₂ | benzyl |
| H | NH₂ | CF=CF₂ |
| H | NH₂ | C₂F₅ |
| H | NH₂ | cyclopropyl |
| H | NH₂ | C₂H₅ |
| H | NH₂ | CF₃O |
| H | NH₂ | F₂CHO |
| H | NH₂ | C₂F₅O |
| H | NH₂ | CF₃S |
| H | NH₂ | F₂CHS |
| H | NH₂ | CF₃ |
| H | NH₂ | CH₃SO |
| H | NH₂ | CH₃SO₂ |
| H | NH₂ | CF₃SO₂ |
| H | NH₂ | O-phenyl |
| H | NH₂ | O-(4-Cl-phenyl) |
| H | CH₃(C=O)NH | O-(3-CF₃-phenyl) |
| H | CH₃(C=O)NH | H |
| H | CH₃(C=O)NH | F |
| H | CH₃(C=O)NH | Cl |
| H | CH₃(C=O)NH | CN |
| H | CH₃(C=O)NH | CH₃ |
| H | CH₃(C=O)NH | CH₃O |
| H | CH₃(C=O)NH | C₂H₅O |
| H | CH₃(C=O)NH | CH₃S |
| H | CH₃(C=O)NH | C₂H₅S |

-continued

| R² | R³ | R⁴ |
|---|---|---|
| H | CH₃(C=O)NH | benzyl |
| H | CH₃(C=O)NH | CF=CF₂ |
| H | CH₃(C=O)NH | C₂F₅ |
| H | CH₃(C=O)NH | cyclopropyl |
| H | CH₃(C=O)NH | C₂H₅ |
| H | CH₃(C=O)NH | CF₃O |
| H | CH₃(C=O)NH | F₂CHO |
| H | CH₃(C=O)NH | C₂F₅O |
| H | CH₃(C=O)NH | CF₃S |
| H | CH₃(C=O)NH | F₂CHS |
| H | CH₃(C=O)NH | CF₃ |
| H | CH₃(C=O)NH | CH₃SO |
| H | CH₃(C=O)NH | CH₃SO₂ |
| H | CH₃(C=O)NH | CF₃SO₂ |
| H | CH₃(C=O)NH | O-phenyl |
| H | CH₃(C=O)NH | O-(4-Cl-phenyl) |
| H | CF₃(C=O)NH | O-(3-CF₃-phenyl) |
| H | CF₃(C=O)NH | H |
| H | CF₃(C=O)NH | F |
| H | CF₃(C=O)NH | Cl |
| H | CF₃(C=O)NH | CN |
| H | CF₃(C=O)NH | CH₃ |
| H | CF₃(C=O)NH | CH₃O |
| H | CF₃(C=O)NH | C₂H₅O |
| H | CF₃(C=O)NH | CH₃S |
| H | CF₃(C=O)NH | C₂H₅S |
| H | CF₃(C=O)NH | benzyl |
| H | CF₃(C=O)NH | CF=CF₂ |
| H | CF₃(C=O)NH | C₂F₅ |
| H | CF₃(C=O)NH | cyclopropyl |
| H | CF₃(C=O)NH | C₂H₅ |
| H | CF₃(C=O)NH | CF₃O |
| H | CF₃(C=O)NH | F₂CHO |
| H | CF₃(C=O)NH | C₂F₅O |
| H | CF₃(C=O)NH | CF₃S |
| H | CF₃(C=O)NH | F₂CHS |
| H | CF₃(C=O)NH | CF₃ |
| H | CF₃(C=O)NH | CH₃SO |
| H | CF₃(C=O)NH | CH₃SO₂ |
| H | CF₃(C=O)NH | CF₃SO₂ |
| H | CF₃(C=O)NH | O-phenyl |
| H | CF₃(C=O)NH | O-(4-Cl-phenyl) |
| H | CH₃NH | O-(3-CF₃-phenyl) |
| H | CH₃NH | H |
| H | CH₃NH | F |
| H | CH₃NH | Cl |
| H | CH₃NH | CN |
| H | CH₃NH | CH₃ |
| H | CH₃NH | CH₃O |
| H | CH₃NH | C₂H₅O |
| H | CH₃NH | CH₃S |
| H | CH₃NH | C₂H₅S |
| H | CH₃NH | benzyl |
| H | CH₃NH | CF=CF₂ |
| H | CH₃NH | C₂F₅ |
| H | CH₃NH | cyclopropyl |
| H | CH₃NH | C₂H₅ |
| H | CH₃NH | CF₃O |
| H | CH₃NH | F₂CHO |
| H | CH₃NH | C₂F₅O |
| H | CH₃NH | CF₃S |
| H | CH₃NH | F₂CHS |
| H | CH₃NH | CF₃ |
| H | CH₃NH | CH₃SO |
| H | CH₃NH | CH₃SO₂ |
| H | CH₃NH | CF₃SO₂ |
| H | CH₃NH | O-phenyl |
| H | CH₃NH | O-(4-Cl-phenyl) |
| H | CH₃CO₂ | O-(3-CF₃-phenyl) |
| H | CH₃CO₂ | H |
| H | CH₃CO₂ | F |
| H | CH₃CO₂ | Cl |
| H | CH₃CO₂ | CN |
| H | CH₃CO₂ | CH₃ |
| H | CH₃CO₂ | CH₃O |
| H | CH₃CO₂ | C₂H₅O |
| H | CH₃CO₂ | CH₃S |
| H | CH₃CO₂ | C₂H₅S |

-continued

| R² | R³ | R⁴ |
|---|---|---|
| H | CH₃CO₂ | benzyl |
| H | CH₃CO₂ | CF=CF₂ |
| H | CH₃CO₂ | C₂F₅ |
| H | CH₃CO₂ | cyclopropyl |
| H | CH₃CO₂ | C₂H₅ |
| H | CH₃CO₂ | CF₃O |
| H | CH₃CO₂ | F₂CHO |
| H | CH₃CO₂ | C₂F₅O |
| H | CH₃CO₂ | CF₃S |
| H | CH₃CO₂ | F₂CHS |
| H | CH₃CO₂ | CF₃ |
| H | CH₃CO₂ | CH₃SO |
| H | CH₃CO₂ | CH₃SO₂ |
| H | CH₃CO₂ | CF₃SO₂ |
| H | CH₃CO₂ | O-phenyl |
| H | CH₃CO₂ | O-(4-Cl-phenyl) |
| H | CF₃CO₂ | O-(3-CF₃-phenyl) |
| H | CF₃CO₂ | H |
| H | CF₃CO₂ | F |
| H | CF₃CO₂ | Cl |
| H | CF₃CO₂ | CN |
| H | CF₃CO₂ | CH₃ |
| H | CF₃CO₂ | CH₃O |
| H | CF₃CO₂ | C₂H₅O |
| H | CF₃CO₂ | CH₃S |
| H | CF₃CO₂ | C₂H₅S |
| H | CF₃CO₂ | benzyl |
| H | CF₃CO₂ | CF=CF₂ |
| H | CF₃CO₂ | C₂F₅ |
| H | CF₃CO₂ | cyclopropyl |
| H | CF₃CO₂ | C₂H₅ |
| H | CF₃CO₂ | CF₃O |
| H | CF₃CO₂ | F₂CHO |
| H | CF₃CO₂ | C₂F₅O |
| H | CF₃CO₂ | CF₃S |
| H | CF₃CO₂ | F₂CHS |
| H | CF₃CO₂ | CF₃ |
| H | CF₃CO₂ | CH₃SO |
| H | CF₃CO₂ | CH₃SO₂ |
| H | CF₃CO₂ | CF₃SO₂ |
| H | CF₃CO₂ | O-phenyl |
| H | CF₃CO₂ | O-(4-Cl-phenyl) |
| H | CF₃SO₂ | O-(3-CF₃-phenyl) |
| H | CF₃SO₂ | H |
| H | CF₃SO₂ | F |
| H | CF₃SO₂ | Cl |
| H | CF₃SO₂ | CN |
| H | CF₃SO₂ | CH₃ |
| H | CF₃SO₂ | CH₃O |
| H | CF₃SO₂ | C₂H₅O |
| H | CF₃SO₂ | CH₃S |
| H | CF₃SO₂ | C₂H₅S |
| H | CF₃SO₂ | benzyl |
| H | CF₃SO₂ | CF=CF₂ |
| H | CF₃SO₂ | C₂F₅ |
| H | CF₃SO₂ | cyclopropyl |
| H | CF₃SO₂ | C₂H₅ |
| H | CF₃SO₂ | CF₃O |
| H | CF₃SO₂ | F₂CHO |
| H | CF₃SO₂ | C₂F₅O |
| H | CF₃SO₂ | CF₃S |
| H | CF₃SO₂ | F₂CHS |
| H | CF₃SO₂ | CF₃ |
| H | CF₃SO₂ | CH₃SO |
| H | CF₃SO₂ | CH₃SO₂ |
| H | CF₃SO₂ | CF₃SO₂ |
| H | CF₃SO₂ | O-phenyl |
| H | CF₃SO₂ | O-(4-Cl-phenyl) |
| F | NO₂ | CH₃ |
| F | NO₂ | CF₃O |
| F | NO₂ | F₂CHO |
| F | NO₂ | C₂F₅O |
| F | NO₂ | CF₃S |
| F | NO₂ | F₂CHS |
| F | NO₂ | CH₃SO |
| F | NO₂ | CH₃SO₂ |
| F | NO₂ | CF₃SO₂ |
| F | NO₂ | O-phenyl |

-continued

| R² | R³ | R⁴ |
|---|---|---|
| F | NO₂ | O-(4-Cl-phenyl) |
| F | NO₂ | ClCF₂O |
| F | NO₂ | i-C₃H₇ |
| F | NO₂ | i-C₄H₉ |
| Cl | NO₂ | O-(3-CF₃-phenyl) |
| Cl | NO₂ | H |
| Cl | NO₂ | F |
| Cl | NO₂ | Cl |
| Cl | NO₂ | CN |
| Cl | NO₂ | CH₃ |
| Cl | NO₂ | CH₃O |
| Cl | NO₂ | C₂H₅O |
| Cl | NO₂ | CH₃S |
| Cl | NO₂ | C₂H₅S |
| Cl | NO₂ | benzyl |
| Cl | NO₂ | CF=CF₂ |
| Cl | NO₂ | C₂F₅ |
| Cl | NO₂ | cyclopropyl |
| Cl | NO₂ | C₂H₅ |
| Cl | NO₂ | CF₃O |
| Cl | NO₂ | F₂CHO |
| Cl | NO₂ | C₂F₅O |
| Cl | NO₂ | CF₃S |
| Cl | NO₂ | F₂CHS |
| Cl | NO₂ | CF₃ |
| Cl | NO₂ | CH₃SO |
| Cl | NO₂ | CH₃SO₂ |
| Cl | NO₂ | CF₃SO₂ |
| Cl | NO₂ | O-phenyl |
| Cl | NO₂ | O-(4-Cl-phenyl) |
| CH₃O | NO₂ | O-(3-CF₃-phenyl) |
| CH₃O | NO₂ | H |
| CH₃O | NO₂ | F |
| CH₃O | NO₂ | Cl |
| CH₃O | NO₂ | CN |
| CH₃O | NO₂ | CH₃ |
| CH₃O | NO₂ | CH₃O |
| CH₃O | NO₂ | C₂H₅O |
| CH₃O | NO₂ | CH₃S |
| CH₃O | NO₂ | C₂H₅S |
| CH₃O | NO₂ | benzyl |
| CH₃O | NO₂ | CF=CF₂ |
| CH₃O | NO₂ | C₂F₅ |
| CH₃O | NO₂ | cyclopropyl |
| CH₃O | NO₂ | C₂H₅ |
| CH₃O | NO₂ | CF₃O |
| CH₃O | NO₂ | F₂CHO |
| CH₃O | NO₂ | C₂F₅O |
| CH₃O | NO₂ | CF₃S |
| CH₃O | NO₂ | F₂CHS |
| CH₃O | NO₂ | CF₃ |
| CH₃O | NO₂ | CH₃SO |
| CH₃O | NO₂ | CH₃SO₂ |
| CH₃O | NO₂ | CF₃SO₂ |
| CH₃O | NO₂ | O-phenyl |
| CH₃O | NO₂ | O-(4-Cl-phenyl) |
| CH₃ | NO₂ | O-(3-CF₃-phenyl) |
| CH₃ | NO₂ | H |
| CH₃ | NO₂ | F |
| CH₃ | NO₂ | Cl |
| CH₃ | NO₂ | CN |
| CH₃ | NO₂ | CH₃ |
| CH₃ | NO₂ | CH₃O |
| CH₃ | NO₂ | C₂H₅O |
| CH₃ | NO₂ | CH₃S |
| CH₃ | NO₂ | C₂H₅S |
| CH₃ | NO₂ | benzyl |
| CH₃ | NO₂ | CF=CF₂ |
| CH₃ | NO₂ | C₂F₅ |
| CH₃ | NO₂ | cyclopropyl |
| CH₃ | NO₂ | C₂H₅ |
| CH₃ | NO₂ | CF₃O |
| CH₃ | NO₂ | F₂CHO |
| CH₃ | NO₂ | C₂F₅O |
| CH₃ | NO₂ | CF₃S |
| CH₃ | NO₂ | F₂CHS |
| CH₃ | NO₂ | CF₃ |
| CH₃ | NO₂ | CH₃SO |
| CH₃ | NO₂ | CH₃SO₂ |
| CH₃ | NO₂ | CF₃SO₂ |
| CH₃ | NO₂ | O-phenyl |
| CH₃ | NO₂ | O-(4-Cl-phenyl) |
| F | NH₂ | C₂H₅ |
| F | NH₂ | CF₃O |
| F | NH₂ | F₂CHO |
| F | NH₂ | C₂H₅O |
| F | NH₂ | CF₃S |
| F | NH₂ | CH₃SO |
| F | NH₂ | CH₃SO₂ |
| F | NH₂ | CF₃SO₂ |
| F | NH₂ | O-phenyl |
| F | NH₂ | O-(4-Cl-phenyl) |
| F | NH₂ | ClCF₂O |
| F | NH₂ | i-C₃H₇ |
| F | NH₂ | CN |
| Cl | CF₃(C=O)NH | O-(3-CF₃-phenyl) |
| Cl | CF₃(C=O)NH | H |
| Cl | CF₃(C=O)NH | F |
| Cl | CF₃(C=O)NH | Cl |
| Cl | CF₃(C=O)NH | CN |
| Cl | CF₃(C=O)NH | CH₃ |
| Cl | CF₃(C=O)NH | CH₃O |
| Cl | CF₃(C=O)NH | C₂H₅O |
| Cl | CF₃(C=O)NH | CH₃S |
| Cl | CF₃(C=O)NH | C₂H₅S |
| Cl | CF₃(C=O)NH | benzyl |
| Cl | CF₃(C=O)NH | CF=CF₂ |
| Cl | CF₃(C=O)NH | C₂F₅ |
| Cl | CF₃(C=O)NH | cyclopropyl |
| Cl | CF₃(C=O)NH | C₂H₅ |
| Cl | CF₃(C=O)NH | CF₃O |
| Cl | CF₃(C=O)NH | F₂CHO |
| Cl | CF₃(C=O)NH | C₂F₅O |
| Cl | CF₃(C=O)NH | CF₃S |
| Cl | CF₃(C=O)NH | F₂CHS |
| Cl | CF₃(C=O)NH | CF₃ |
| Cl | CF₃(C=O)NH | CH₃SO |
| Cl | CF₃(C=O)NH | CH₃SO₂ |
| Cl | CF₃(C=O)NH | CF₃SO₂ |
| Cl | CF₃(C=O)NH | O-phenyl |
| Cl | CF₃(C=O)NH | O-(4-Cl-phenyl) |
| Cl | CH₃NH | O-(3-CF₃-phenyl) |
| Cl | CH₃NH | H |
| Cl | CH₃NH | F |
| Cl | CH₃NH | Cl |
| Cl | CH₃NH | CN |
| Cl | CH₃NH | CH₃ |
| Cl | CH₃NH | CH₃O |
| Cl | CH₃NH | C₂H₅O |
| Cl | CH₃NH | CH₃S |
| Cl | CH₃NH | C₂H₅S |
| Cl | CH₃NH | benzyl |
| Cl | CH₃NH | CF=CF₂ |
| Cl | CH₃NH | C₂F₅ |
| Cl | CH₃NH | cyclopropyl |
| Cl | CH₃NH | C₂H₅ |
| Cl | CH₃NH | CF₃O |
| Cl | CH₃NH | F₂CHO |
| Cl | CH₃NH | C₂F₅O |
| Cl | CH₃NH | CF₃S |
| Cl | CH₃NH | F₂CHS |
| Cl | CH₃NH | CF₃ |
| Cl | CH₃NH | CH₃SO |
| Cl | CH₃NH | CH₃SO₂ |
| Cl | CH₃NH | CF₃SO₂ |
| Cl | CH₃NH | O-phenyl |
| Cl | CH₃NH | O-(4-Cl-phenyl) |
| CH₃ | CF₃(C=O)NH | O-(3-CF₃-phenyl) |
| CH₃ | CF₃(C=O)NH | H |
| CH₃ | CF₃(C=O)NH | F |
| CH₃ | CF₃(C=O)NH | Cl |
| CH₃ | CF₃(C=O)NH | CN |
| CH₃ | CF₃(C=O)NH | CH₃ |
| CH₃ | CF₃(C=O)NH | CH₃O |
| CH₃ | CF₃(C=O)NH | C₂H₅O |
| CH₃ | CF₃(C=O)NH | CH₃S |

| R² | R³ | R⁴ |
|---|---|---|
| CH₃ | CF₃(C=O)NH | C₂H₅S |
| CH₃ | CF₃(C=O)NH | benzyl |
| CH₃ | CF₃(C=O)NH | CF=CF₂ |
| CH₃ | CF₃(C=O)NH | C₂F₅ |
| CH₃ | CF₃(C=O)NH | cyclopropyl |
| CH₃ | CF₃(C=O)NH | C₂H₅ |
| CH₃ | CF₃(C=O)NH | CF₃O |
| CH₃ | CF3 (C=O)NH | F₂CHO |
| CH₃ | CF3 (C=O)NH | C₂F₅O |
| CH₃ | CF₃(C=O)NH | CF₃S |
| CH₃ | CF₃(C=O)NH | F₂CHS |
| CH₃ | CF₃(C=O)NH | CF₃ |
| CH₃ | CF₃(C=O)NH | CH₃SO |
| CH₃ | CF₃(C=O)NH | CH₃SO₂ |
| CH₃ | CF₃(C=O)NH | CF₃SO₂ |
| CH₃ | CF₃(C=O)NH | O-phenyl |
| CH₃ | CF₃(C=O)NH | O-(4-Cl-phenyl) |
| CH₃O | NH₂ | O-(3-CF₃-phenyl) |
| CH₃O | NH₂ | H |
| CH₃O | NH₂ | F |
| CH₃O | NH₂ | Cl |
| CH₃O | NH₂ | CN |
| CH₃O | NH₂ | CH₃ |
| CH₃O | NH₂ | CH₃O |
| CH₃O | NH₂ | C₂H₅O |
| CH₃O | NH₂ | CH₃S |
| CH₃O | NH₂ | C₂H₅S |
| CH₃O | NH₂ | benzyl |
| CH₃O | NH₂ | CF=CF₂ |
| CH₃O | NH₂ | C₂F₅ |
| CH₃O | NH₂ | cyclopropyl |
| CH₃O | NH₂ | C₂H₅ |
| CH₃O | NH₂ | CF₃O |
| CH₃O | NH₂ | F₂CHO |
| CH₃O | NH₂ | C₂F₅O |
| CH₃O | NH₂ | CF₃S |
| CH₃O | NH₂ | F₂CHS |
| CH₃O | NH₂ | CF₃ |
| CH₃O | NH₂ | CH₃SO |
| CH₃O | NH₂ | CH₃SO₂ |
| CH₃O | NH₂ | CF₃SO₂ |
| CH₃O | NH₂ | O-phenyl |
| CH₃O | NH₂ | O-(4-Cl-phenyl) |
| CH₃O | CF₃(C=O)NH | O-(3-CF₃-phenyl) |
| CH₃O | CF₃(C=O)NH | H |
| CH₃O | CF₃(C=O)NH | F |
| CH₃O | CF₃(C=O)NH | Cl |
| CH₃O | CF₃(C=O)NH | CN |
| CH₃O | CF₃(C=O)NH | CH₃ |
| CH₃O | CF₃(C=O)NH | CH₃O |
| CH₃O | CF₃(C=O)NH | C₂H₅O |
| CH₃O | CF₃(C=O)NH | CH₃S |
| CH₃O | CF₃(C=O)NH | C₂H₅S |
| CH₃O | CF₃(C=O)NH | benzyl |
| CH₃O | CF₃(C=O)NH | CF=CF₂ |
| CH₃O | CF₃(C=O)NH | C₂F₅ |
| CH₃O | CF₃(C=O)NH | cyclopropyl |
| CH₃O | CF₃(C=O)NH | C₂H₅ |
| CH₃O | CF₃(C=O)NH | CF₃O |
| CH₃O | CF₃(C=O)NH | F₂CHO |
| CH₃O | CF₃(C=O)NH | C₂F₅O |
| CH₃O | CF₃(C=O)NH | CF₃S |
| CH₃O | CF₃(C=O)NH | F₂CHS |
| CH₃O | CF₃(C=O)NH | CF₃ |
| CH₃O | CF₃(C=O)NH | CH₃SO |
| CH₃O | CF₃(C=O)NH | CH₃SO₂ |
| CH₃O | CF₃(C=O)NH | CF₃SO₂ |
| CH₃O | CF₃(C=O)NH | O-phenyl |
| CH₃O | CF₃(C=O)NH | O-(4-Cl-phenyl) |
| CH₃ | NH₂ | O-(3-CF₃-phenyl) |
| CH₃ | NH₂ | H |
| CH₃ | NH₂ | F |
| CH₃ | NH₂ | Cl |
| CH₃ | NH₂ | CN |
| CH₃ | NH₂ | CH₃ |
| CH₃ | NH₂ | CH₃O |
| CH₃ | NH₂ | C₂H₅O |
| CH₃ | NH₂ | CH₃S |

| R² | R³ | R⁴ |
|---|---|---|
| CH₃ | NH₂ | C₂H₅S |
| CH₃ | NH₂ | benzyl |
| CH₃ | NH₂ | CF=CF₂ |
| CH₃ | NH₂ | C₂F₅ |
| CH₃ | NH₂ | cyclopropyl |
| CH₃ | NH₂ | C₂H₅ |
| CH₃ | NH₂ | CF₃O |
| CH₃ | NH₂ | F₂CHO |
| CH₃ | NH₂ | C₂F₅O |
| CH₃ | NH₂ | CF₃S |
| CH₃ | NH₂ | F₂CHS |
| CH₃ | NH₂ | CF₃ |
| CH₃ | NH₂ | CH₃SO |
| CH₃ | NH₂ | CH₃SO₂ |
| CH₃ | NH₂ | CF₃SO₂ |
| CH₃ | NH₂ | O-phenyl |
| CH₃ | NH₂ | O-(4-Cl-phenyl) |
| Cl | NH₂ | O-(3-CF₃-phenyl) |
| Cl | NH₂ | H |
| Cl | NH₂ | F |
| Cl | NH₂ | Cl |
| Cl | NH₂ | CN |
| Cl | NH₂ | CH₃ |
| Cl | NH₂ | CH₃O |
| Cl | NH₂ | C₂H₅O |
| Cl | NH₂ | CH₃S |
| Cl | NH₂ | C₂H₅S |
| Cl | NH₂ | benzyl |
| Cl | NH₂ | CF=CF₂ |
| Cl | NH₂ | C₂F₅ |
| Cl | NH₂ | cyclopropyl |
| Cl | NH₂ | C₂H₅ |
| Cl | NH₂ | CF₃O |
| Cl | NH₂ | F₂CHO |
| Cl | NH₂ | C₂F₅O |
| Cl | NH₂ | CF₃S |
| Cl | NH₂ | F₂CHS |
| Cl | NH₂ | CF₃ |
| Cl | NH₂ | CH₃SO |
| Cl | NH₂ | CH₃SO₂ |
| Cl | NH₂ | CF₃SO₂ |
| Cl | NH₂ | O-phenyl |
| Cl | NH₂ | O-(4-Cl-phenyl) |
| NH₂ | NO₂ | O-(3-CF₃-phenyl) |
| NH₂ | NO₂ | H |
| NH₂ | NO₂ | F |
| NH₂ | NO₂ | Cl |
| NH₂ | NO₂ | CN |
| NH₂ | NO₂ | CH₃ |
| NH₂ | NO₂ | CH₃O |
| NH₂ | NO₂ | C₂H₅O |
| NH₂ | NO₂ | CH₃S |
| NH₂ | NO₂ | C₂H₅S |
| NH₂ | NO₂ | benzyl |
| NH₂ | NO₂ | CF=CF₂ |
| NH₂ | NO₂ | C₂F₅ |
| NH₂ | NO₂ | cyclopropyl |
| NH₂ | NO₂ | C₂H₅ |
| NH₂ | NO₂ | CF₃O |
| NH₂ | NO₂ | F₂CHO |
| NH₂ | NO₂ | C₂F₅O |
| NH₂ | NO₂ | CF₃S |
| NH₂ | NO₂ | F₂CHS |
| NH₂ | NO₂ | CF₃ |
| NH₂ | NO₂ | CH₃SO |
| NH₂ | NO₂ | CH₃SO₂ |
| NH₂ | NO₂ | CF₃SO₂ |
| NH₂ | NO₂ | O-phenyl |
| NH₂ | NO₂ | O-(4-Cl-phenyl) |
| NH₂ | Cl | O-(3-CF₃-phenyl) |
| NH₂ | Cl | H |
| NH₂ | Cl | F |
| NH₂ | Cl | Cl |
| NH₂ | Cl | CN |
| NH₂ | Cl | CH₃ |
| NH₂ | Cl | CH₃O |
| NH₂ | Cl | C₂H₅O |
| NH₂ | Cl | CH₃S |

| R² | R³ | R⁴ |
|---|---|---|
| NH₂ | Cl | C₂H₅S |
| NH₂ | Cl | benzyl |
| NH₂ | Cl | CF=CF₂ |
| NH₂ | Cl | C₂F₅ |
| NH₂ | Cl | cyclopropyl |
| NH₂ | Cl | C₂H₅ |
| NH₂ | Cl | CF₃O |
| NH₂ | Cl | F₂CHO |
| NH₂ | Cl | C₂F₅O |
| NH₂ | Cl | CF₃S |
| NH₂ | Cl | F₂CHS |
| NH₂ | Cl | CF₃ |
| NH₂ | Cl | CH₃SO |
| NH₂ | Cl | CH₃SO₂ |
| NH₂ | Cl | CF₃SO₂ |
| NH₂ | Cl | O-phenyl |
| NH₂ | Cl | O-(4-Cl-phenyl) |
| NH₂ | NH₂ | O-(3-CF₃-phenyl) |
| NH₂ | NH₂ | H |
| NH₂ | NH₂ | F |
| NH₂ | NH₂ | Cl |
| NH₂ | NH₂ | CN |
| NH₂ | NH₂ | CH₃ |
| NH₂ | NH₂ | CH₃O |
| NH₂ | NH₂ | C₂H₅O |
| NH₂ | NH₂ | CH₃S |
| NH₂ | NH₂ | C₂H₅S |
| NH₂ | NH₂ | benzyl |
| NH₂ | NH₂ | CF=CF₂ |
| NH₂ | NH₂ | C₂F₅ |
| NH₂ | NH₂ | cyclopropyl |
| NH₂ | NH₂ | C₂H₅ |
| NH₂ | NH₂ | CF₃O |
| NH₂ | NH₂ | F₂CHO |
| NH₂ | NH₂ | C₂F₅O |
| NH₂ | NH₂ | CF₃S |
| NH₂ | NH₂ | F₂CHS |
| NH₂ | NH₂ | CF₃ |
| NH₂ | NH₂ | CH₃SO |
| NH₂ | NH₂ | CH₃SO₂ |
| NH₂ | NH₂ | CF₃SO₂ |
| NH₂ | NH₂ | O-phenyl |
| NH₂ | NH₂ | O-(4-Cl-phenyl) |
| NH₂ | CF₃(C=O)NH | O-(3-CF₃-phenyl) |
| NH₂ | CF₃(C=O)NH | H |
| NH₂ | CF₃(C=O)NH | F |
| NH₂ | CF₃(C=O)NH | Cl |
| NH₂ | CF₃(C=O)NH | CN |
| NH₂ | CF₃(C=O)NH | CH₃ |
| NH₂ | CF₃(C=O)NH | CH₃O |
| NH₂ | CF₃(C=O)NH | C₂H₅O |
| NH₂ | CF₃(C=O)NH | CH₃S |
| NH₂ | CF₃(C=O)NH | C₂H₅S |
| NH₂ | CF₃(C=O)NH | benzyl |
| NH₂ | CF₃(C=O)NH | CF=CF₂ |
| NH₂ | CF₃(C=O)NH | C₂F₅ |
| NH₂ | CF₃(C=O)NH | cyclopropyl |
| NH₂ | CF₃(C=O)NH | C₂H₅ |
| NH₂ | CF₃(C=O)NH | CF₃O |
| NH₂ | CF₃(C=O)NH | F₂CHO |
| NH₂ | CF₃(C=O)NH | C₂F₅O |
| NH₂ | CF₃(C=O)NH | CF₃S |
| NH₂ | CF₃(C=O)NH | F₂CHS |
| NH₂ | CF₃(C=O)NH | CF₃ |
| NH₂ | CF₃(C=O)NH | CH₃SO |
| NH₂ | CF₃(C=O)NH | CH₃SO₂ |
| NH₂ | CF₃(C=O)NH | CF₃SO₂ |
| NH₂ | CF₃(C=O)NH | O-phenyl |
| NH₂ | CF₃(C=O)NH | O-(4-Cl-phenyl) |
| CF₃(C=O)NH | Cl | O-(3-CF₃-phenyl) |
| CF₃(C=O)NH | Cl | H |
| CF₃(C=O)NH | Cl | F |
| CF₃(C=O)NH | Cl | Cl |
| CF₃(C=O)NH | Cl | CN |
| CF₃(C=O)NH | Cl | CH₃ |
| CF₃(C=O)NH | Cl | CH₃O |
| CF₃(C=O)NH | Cl | C₂H₅O |
| CF₃(C=O)NH | Cl | CH₃S |
| CF₃(C=O)NH | Cl | C₂H₅S |
| CF₃(C=O)NH | Cl | benzyl |
| CF₃(C=O)NH | Cl | CF=CF₂ |
| CF₃(C=O)NH | Cl | C₂F₅ |
| CF₃(C=O)NH | Cl | cyclopropyl |
| CF₃(C=O)NH | Cl | C₂H₅ |
| CF₃(C=O)NH | Cl | CF₃O |
| CF₃(C=O)NH | Cl | F₂CHO |
| CF₃(C=O)NH | Cl | C₂F₅O |
| CF₃(C=O)NH | Cl | CF₃S |
| CF₃(C=O)NH | Cl | F₂CHS |
| CF₃(C=O)NH | Cl | CF₃ |
| CF₃(C=O)NH | Cl | CH₃SO |
| CF₃(C=O)NH | Cl | CH₃SO₂ |
| CF₃(C=O)NH | Cl | CF₃SO₂ |
| CF₃(C=O)NH | Cl | O-phenyl |
| CF₃(C=O)NH | Cl | O-(4-Cl-phenyl) |
| CF₃(C=O)NH | CH₃ | O-(3-CF₃-phenyl) |
| CF₃(C=O)NH | CH₃ | H |
| CF₃(C=O)NH | CH₃ | F |
| CF₃(C=O)NH | CH₃ | Cl |
| CF₃(C=O)NH | CH₃ | CN |
| CF₃(C=O)NH | CH₃ | CH₃ |
| CF₃(C=O)NH | CH₃ | CH₃O |
| CF₃(C=O)NH | CH₃ | C₂H₅O |
| CF₃(C=O)NH | CH₃ | CH₃S |
| CF₃(C=O)NH | CH₃ | C₂H₅S |
| CF₃(C=O)NH | CH₃ | benzyl |
| CF₃(C=O)NH | CH₃ | CF=CF₂ |
| CF₃(C=O)NH | CH₃ | C₂F₅ |
| CF₃(C=O)NH | CH₃ | cyclopropyl |
| CF₃(C=O)NH | CH₃ | C₂H₅ |
| CF₃(C=O)NH | CH₃ | CF₃O |
| CF₃(C=O)NH | CH₃ | F₂CHO |
| CF₃(C=O)NH | CH₃ | C₂F₅O |
| CF₃(C=O)NH | CH₃ | CF₃S |
| CF₃(C=O)NH | CH₃ | F₂CHS |
| CF₃(C=O)NH | CH₃ | CF₃ |
| CF₃(C=O)NH | CH₃ | CH₃SO |
| CF₃(C=O)NH | CH₃ | CH₃SO₂ |
| CF₃(C=O)NH | CH₃ | CF₃SO₂ |
| CF₃(C=O)NH | CH₃ | O-phenyl |
| CF₃(C=O)NH | CH₃ | O-(4-Cl-phenyl) |
| CF₃(C=O)NH | CH₃O | O-(3-CF₃-phenyl) |
| CF₃(C=O)NH | CH₃O | H |
| CF₃(C=O)NH | CH₃O | F |
| CF₃(C=O)NH | CH₃O | Cl |
| CF₃(C=O)NH | CH₃O | CN |
| CF₃(C=O)NH | CH₃O | CH₃ |
| CF₃(C=O)NH | CH₃O | CH₃O |
| CF₃(C=O)NH | CH₃O | C₂H₅O |
| CF₃(C=O)NH | CH₃O | CH₃S |
| CF₃(C=O)NH | CH₃O | C₂H₅S |
| CF₃(C=O)NH | CH₃O | benzyl |
| CF₃(C=O)NH | CH₃O | CF=CF₂ |
| CF₃(C=O)NW | CH₃O | C₂F₅ |
| CF₃(C=O)NH | CH₃O | cyclopropyl |
| CF₃(C=O)NH | CH₃O | C₂H₅ |
| CF₃(C=O)NH | CH₃O | CF₃O |
| CF₃(C=O)NH | CH₃O | F₂CHO |
| CF₃(C=O)NH | CH₃O | C₂F₅O |
| CF₃(C=O)NH | CH₃O | CF₃S |
| CF₃(C=O)NH | CH₃O | F₂CHS |
| CF₃(C=O)NH | CH₃O | CF₃ |
| CF₃(C=O)NH | CH₃O | CH₃SO |
| CF₃(C=O)NH | CH₃O | CH₃SO₂ |
| CF₃(C=O)NH | CH₃O | CF₃SO₂ |
| CF₃(C=O)NH | CH₃O | O-phenyl |
| CF₃(C=O)NH | CH₃O | O-(4-Cl-phenyl) |
| Cl | Cl | NO₂ |
| CH₃ | Cl | NO₂ |
| Cl | CH₃ | NO₂ |
| CH₃O | Cl | NO₂ |
| Cl | CH₃O | NO₂ |
| CH₃ | CH₃ | NO₂ |
| NH₂ | Cl | NO₂ |
| CF₃(C=O)NH | Cl | NO₂ |
| Cl | Cl | OH |

| R² | R³ | R⁴ |
| --- | --- | --- |
| CH₃ | Cl | OH |
| Cl | CH₃ | OH |
| CH₃ | CH₃ | OH |
| CH₃O | Cl | OH |
| Cl | CH₃O | OH |
| Cl | Cl | CH₃CO₂ |
| CH₃ | Cl | CH₃CO₂ |
| Cl | CH₃ | CH₃CO₂ |
| CH₃ | CH₃ | CH₃CO₂ |
| CH₃O | Cl | CH₃CO₂ |
| Cl | CH₃O | CH₃CO₂ |
| CH₃CO₂ | Cl | Cl |
| CH₃CO₂ | CH₃ | Cl |
| CH₃CO₂ | Cl | CH₃ |
| CH₃CO₂ | Cl | CH₃O |
| Cl | CH₃CO₂ | Cl |
| CH₃ | CH₃CO₂ | Cl |
| Cl | Cl | CF₃CO₂ |
| Cl | CH₃ | CF₃CO₂ |
| Cl | Cl | NH₂ |
| CH₃ | Cl | NH₂ |
| Cl | CH₃ | NH₂ |
| CH₃ | CH₃ | NH₂ |
| CH₃O | Cl | NH₂ |
| Cl | CH₃O | NH₂ |
| Cl | Cl | CF₃(C=O)NH |
| CH₃ | Cl | CF₃(C=O)NH |
| Cl | CH₃ | CF₃(C=O)NH |
| CH₃O | Cl | CF₃(C=O)NH |
| Cl | CH₃O | CF₃(C=O)NH |
| CF₃CO₂ | Cl | H |
| CF₃CO₂ | CH₃ | H |
| CF₃CO₂ | CH₃ | Cl |
| CF₃CO₂ | Cl | CH₃ |
| C₆H₅CH₂NH | H | H |
| C₆H₅CH₂NH | Cl | H |
| CH₃ | Cl | C₆H₅CH₂NH |
| CH₃O | Cl | C₆H₅CH₂NH |

Preferred definitions of R¹ are:

| No. | R¹ |
| --- | --- |
| L1 | OCH₃ |
| L2 | OC₂H₅ |
| L3 | O-i-C₃H₇ |
| L4 | n-C₃H₇ |
| L5 | i-C₃H₇ |
| L6 | n-C₄H₉ |
| L7 | i-C₄H₉ |
| L8 | sec-C₄H₉ |
| L9 | tert-C₄H₉ |
| L10 | n-C₅H₁₁ |
| L11 | —CH(CH₃)C₃H₇ |
| L12 | —CH(C₂H₅)C₂H₅ |
| L13 | n-C₆H₁₃ |
| L14 | —CH(CH₃)C₄H₉ |
| L15 | —CH(C₂H₅)C₃H₇ |
| L16 | OC(CH₃)₃ |
| L17 | cyclo-C₃H₅ |
| L18 | cyclo-C₄H₇ |
| L19 | cyclo-C₅H₉ |
| L20 | cyclo-C₆H₁₁ |
| L21 | cyclo-C₇H₁₃ |
| L22 | cyclo-C₈H₁₅ |
| L23 | 1-methylcyclohexyl |
| L24 | 1-ethylcyclohexyl |
| L25 | 3,5-dimethylcyclohexyl |
| L26 | 3-trifluoromethylcyclohexyl |
| L27 | 1-(cyclopropyl)ethyl |
| L28 | 1-(cyclopentyl)ethyl |
| L29 | 1-(cyclohexyl)ethyl |
| L30 | —CH₂—CH=CH₂ |
| L31 | —CH(CH₃)CH=CH₂ |
| L32 | —C(CH₃)₂CH=CH₂ |
| L33 | —C(CH₃, C₂H₅)CH=CH₂ |
| L34 | —C(CH₃)₂—C₂H₅ |
| L35 | —C(CH₃, C₂H₅)C₂H₅ |
| L36 | —C(CH₃)₂C₃H₇ |
| L37 | —C(CH₃)₂cycloC₆H₁₁ |
| L38 | —CH₂—C(CH₃)=CH₂ |
| L39 | —CH₂CH=CHCH₃ |
| L40 | —CH(CH₃)CH=CHCH₃ |
| L41 | —C(CH₃)₂CH=CHCH₃ |
| L42 | —CH₂C≡CH |
| L43 | —CH(CH₃)C≡CH |
| L44 | —C(CH₃)₂C≡CH |
| L45 | —C(CH₃, C₂H₅)C≡CH |
| L46 | —C(C₂H₅)₂C≡CH |
| L47 | —CH₂C≡CCH₃ |
| L48 | —CH(CH₃)C≡CCH₃ |
| L49 | —C(CH₃)₂C≡CCH₃ |
| L50 | —CH(CH₃)CH₂SCH₃ |
| L51 | —C(CH₃)₂CH₂SCH₃ |
| L52 | —CH₂CH₂CH₂SCH₃ |
| L53 | —CH(CH₃)CH₂Cl |
| L54 | —C(CH₃)₂CH₂Cl |
| L55 | —CH(CH₃)CH₂OCH₃ |
| L56 | —C(CH₃)₂CH₂OCH₃ |
| L57 | —CH₂CH₂CH₂OCH₃ |
| L58 | —CH₂CH₂CH₂N(CH₃)₂ |
| L59 | —CH₂CH₂CH₂N(C₂H₅)₂ |
| L60 | cyclopropylmethyl |
| L61 | C(CH₃)₂CH₂F |
| L62 | H |
| L63 | CH₃ |
| L64 | C₂H₅ |
| L65 | 1-methylcyclopropyl |
| L66 | 1-ethylcyclopropyl |

The compounds I or the herbicidal compositions containing them and their environmentally tolerable salts eg. of alkali metals and alkaline earth metals can very effectively control broad-leafed weeds and grass weeds in crops such as wheat, rice, maize, soybeans and cotton without damaging the crop plants, an effect which occurs especially even at low application rates.

The compounds I or the herbicidal compositions containing them can be applied by spraying, atomizing, dusting, broadcasting or watering, for example, in the form of directly sprayable aqueous solutions, powders, suspensions, even high-percentage aqueous, oily or other suspensions or dispersions, emulsions, oil dispersions, pastes, dusting compositions, broadcasting compositions or granules. The application forms depend on the intended uses; in each case they should if possible ensure the finest dispersion of the active compounds according to the invention.

The compounds I are generally suitable for preparing directly sprayable solutions, emulsions, pastes or oil dispersions. Suitable inert additives are mineral oil fractions of medium to high boiling point, such as kerosene or diesel oil, additionally coal tar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, methanol, ethanol, propanol, butanol, cyclohexanol, cyclohexanone or strongly polar solvents, such as N-methylpyrrolidone or water.

Aqueous application forms can be prepared from emulsion concentrates, suspensions, pastes, wettable powders or water-dispersible granules by addition of water. To prepare emulsions, pastes or oil dispersions, the substrates as such or dissolved in an oil or solvent can be homogenized in water by means of wetting agents, adhesives, dispersants or emulsifiers. However, concentrates consisting of active substance, wetting agent, adhesive, dispersant or emulsifier and possibly solvent or oil can also be prepared, which are suitable for dilution with water.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols and of fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ether, ethoxylated isooctyl-, octyl- or nonylphenol, alkylphenol or tributylphenol polyglycol ethers, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the active substances with a solid carrier.

Granules, eg. coated, impregnated and homogeneous granules, can be prepared by binding the active compounds to solid carriers. Solid carriers are mineral earths such as silica gel, silicic acids, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products such as cereal flour, tree bark meal, wood meal and nutshell meal, cellulose powder or other solid carriers.

The formulations in general contain from 0.01 to 95% by weight, preferably from 0.5 to 90% by weight, of active compound. The active compounds are employed here in a purity of from 90% to 100%, preferably from 95% to 100% (by NMR spectrum).

The compounds I according to the invention can be formulated, for example, as follows:

I. 20 parts by weight of the compound No. 1.001 are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II. 20 parts by weight of the compound No. 1.004 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III. 20 parts by weight of the active compound No. 1.006 are dissolved in a mixture which consists of 25 parts by weight of cyclohexanone, 65 parts by weight of a mineral oil fraction of boiling point 210 to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV. 20 parts by weight of the active compound No. 1.016 are well mixed with 3 parts by weight of the sodium salt of diisobutylnaphthalene α-sulfonic acid, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray mixture is obtained which contains 0.1% by weight of the active compound.

V. 3 parts by weight of the active compound No. 1.018 are mixed with 97 parts by weight of finely divided kaolin. In this way a dusting composition is obtained which contains 3% by weight of the active compound.

VI. 20 parts by weight of the active compound No. 1.023 are intimately mixed with 2 parts by weight of calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

The application of the herbicidal compositions or of the active compounds can be carried out pre-emergence or post-emergence. If the active compounds are less tolerable for certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

Depending on the target of control, time of year, target plants and stage of growth, the application rates of active compound are from 0.01 to 5.0, preferably from 0.05 to 2.0, kg/ha of active substance (a.s.).

In consideration of the variety of application methods, the compounds I according to the invention or compositions containing them can additionally be employed in a further number of crop plants for the elimination of undesired plants. Suitable crops are, for example, the following:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum (N. rustica), Olea europaea, Oryza sativa, Phaseolus lunatus, Phaseolus vulgaris, Picea abies, Pinus* spp., *Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.*

To broaden the spectrum of action and to achieve synergistic effects, the pyridine-2,3-dicarboximides I can be mixed and applied together with numerous representatives of other herbicidal or growth-regulating active compound groups. For example, suitable herbicidal mixing components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which in the 2-position carry, eg. a carboxyl or carbimino group, quinolinecarboxylic acid derivatives, imidazolines, sulfonamides, sulfonylureas, aryloxy- or heteroaryloxyphenoxypropionic acids and their salts, esters and amides and others.

It may additionally be useful to apply the compounds I on their own, or together, mixed in a combination with other herbicides or growth regulators and additionally with further crop protection agents, for example with agents for controlling pests or phytogenic fungi or bacteria. Also of interest is the miscibility with mineral salt solutions, which can be employed for the elimination of nutritional and trace element deficiencies. Non-phytotoxic 30 oils and oil concentrates may also be added.

A) Preparation of precursors

Diethyl 5-nitropyridine-2,3-dicarboxylate 255 ml of acetic anhydride were added to a mixture of 203.2 g (0.85 mol) of diethyl pyridine-2,3-dicarboxylate-N-oxide in 1.2 l of glacial acetic acid. 68.3 g (1.06 mol) of 98% strength nitric acid were then added in the course of 40 minutes at from 20 to 28° C. with gentle cooling and stirring and the mixture was stirred at 30° C. for 12 hours. The reaction solution was poured into 3.5 l of ice-water and extracted with methylene chloride. The organic phase was extracted in succession with water, saturated sodium hydrogencarbonate solution and sodium chloride solution, dried over magnesium sulfate and filtered off with suction through silica gel. After concentration, 177.6 g (78% of theory) of diethyl 5-nitropyridine-2,3-dicarboxylate-N-oxide were obtained of $n_D^{25}=1.5290$. A sample crystallized after relatively long standing; m.p. 84–86° C.

88.8 g (0.648 mol) of phosphorus trichloride were added in the course of 30 minutes while stirring at 25° C. to a mixture of 92 g (0.324 mol) of the above N-oxide and 300 ml of 1,2-dichloroethane. After stirring at 25° C. for 12 hours, the reaction mixture was concentrated in vacuo, the residue was taken up again in methylene chloride and the solution was poured into 2.5 l of ice-water. After phase separation, the aqueous phase was extracted with methylene chloride. The organic extract was washed with water, saturated sodium hydrogencarbonate and sodium chloride solution, dried over magnesium sulfate and filtered off with suction through neutral alumina and silica gel. After concentrating, 58.2 g (67% of theory) of the title compound were obtained as a yellowish syrup.

$^1$H-NMR, 400 MHz (CDCl$_3$) δ: Ar 9.0 (d/1H), 9.55 (d,1H)

5-Nitropyridine-2,3-dicarboxylic anhydride 45 g (0.168 mol) of diethyl 5-nitropyridine-2,3-dicarboxylate were added in the course of 10 minutes with stirring to a mixture of 13.4 g (0.336 mol) of sodium hydroxide in 65 ml of water and washed in with 6.5 ml of ethanol. The mixture was brought to reflux, diluted with a further 30 ml of water and cooled again after heating for 1 hour. The precipitate deposited after the addition of 500 ml of acetone was filtered off with suction, washed and dried, 42.4 g (98.6% of theory) of sodium 5-nitropyridine-2,3-dicarboxylate of m.p. >260° C. being obtained.

This was initially introduced in 500 ml of 1,2-dichloroethane and combined with 39 g (0.497 mol) of acetyl chloride in the course of 15 minutes. The reaction mixture was stirred under reflux for 4 hours and cooled, and the precipitate deposited was separated off and washed with methylene chloride. After concentrating in vacuo, triturating the residue with ether/pentane, filtering off with suction and drying, 25.4 g (79% of theory) of the title compound of m.p. 85–91° C. were obtained.

Diethyl 5-aminopyridine-2,3-dicarboxylate 17 g (0.060 mol) of diethyl 5-nitropyridine-2,3-dicarboxylate-N-oxide in 200 ml of glacial acetic acid were added to a mixture of 10.7 g (0.19 mol) of iron powder in 50 ml of glacial acetic acid at 70° C. with stirring in the course of 20 minutes. After stirring at 70° C. for 1 hour, the reaction mixture was cooled, and the precipitate was filtered off with suction and washed with ethyl acetate. The filtrate was concentrated under reduced pressure, dissolved in methylene chloride, washed with water and with saturated sodium chloride solution, dried over magnesium sulfate and filtered off with suction through silica gel. After concentrating under reduced pressure, 11 g (77% of theory) of the title compound were obtained as a semisolid mass.

$^1$H-NMR, 270 MHz (CDCl$_3$) δ: Ar 7.08 (d/1), 8.15 (d, 1), NH$_2$ 4.45 (s/2)

Diethyl 6-chloro-5-nitropyridine-2,3-dicarboxylate 100 g (0.352 mol) of diethyl 5-nitropyridine-2,3-dicarboxylate were added to 500 ml of phosphoryl chloride in the course of 15 minutes with stirring at 60° C., heated to reflux and stirred for 1½ hours. After cooling, the reaction mixture was concentrated under reduced pressure and the residue dissolved again in methylene chloride. After stirring with ice-water, the aqueous phase was washed again with methylene chloride and the organic extracts were then washed in succession with water, saturated sodium hydrogencarbonate and sodium chloride solution and dried over magnesium sulfate. After filtering off with suction through neutral alumina and concentrating, 68.8 g (64.6% of theory) of the title compound of m.p. 70–72° C. were obtained.

(Not claimed according to the invention)

Diethyl 6-benzylaminopyridine-2,3-dicarboxylate 10.7 g (0.1 mol) of benzylamine and 10.1 g (0.1 mol) of triethylamine were added to a mixture of 25.8 g (0.1 mol) of diethyl 6-chloropyridine-2,3-dicarboxylate in 250 ml of propanol at 25° C. with stirring in the course of 10 minutes. After stirring under reflux for 12 hours, the reaction mixture was concentrated, the residue was taken up in methylene chloride and the solution was extracted with water. The organic phase was dried, filtered off with suction through neutral alumina and concentrated under reduced pressure. The residue was stirred in ether/pentane, filtered off with suction and dried, 23.3 g (71.1% of theory) of the title compound of m.p. 110–114° C. being obtained.

Diethyl 5-trifluoroacetamidopyridine-2,3-dicarboxylate 23.8 g (0.114 mol) of trifluoroacetic anhydride were added to a mixture of 10.8 g (0.045 mol) of diethyl 5-aminopyridine-2,3-dicarboxylate in 100 ml of 1,2-dichloroethane with stirring at 25° C. in the course of 10 minutes and refluxed for 3 hours. The reaction mixture was introduced into 500 ml of ice-water and extracted three times with methylene chloride.

The organic extract was washed with water, saturated sodium hydrogencarbonate and a sodium chloride solution and dried over magnesium sulfate. After concentrating under reduced pressure, 14.6 g (96% of theory) of the title compound were obtained as a colorless syrup of $n_D^{25}=1.5018$.

$^1$H-NMR, 200 MHz (CDCl$_3$) δ: Ar 8.63 (s/1), 8.95 (s,1), NH 11.25 (s/1)

B) Preparation of the final products I

N-1-(Cyclopropyl)ethyl-5-nitropyridine-2,3-dicarboximide 11.2 g (0.132 mol) of 1-cyclopropylethylamine were added to a mixture of 22.3 g (0.115 mol) of 5-nitropyridine-2,3-dicarboxylic anhydride in 150 ml of 1,2-dichloroethane at 25a° C with stirring in the course of 8 minutes and the mixture was stirred at 70° C. for 3 hours. After cooling to 25° C., 19.6 g (0.165 mol) of thionyl chloride were added with stirring in the course of 10 minutes and the mixture was stirred at 25° C. for 10 hours and at 70° C for 1½ hours. The reaction mixture was diluted with 100 ml of methylene chloride and added with stirring to 500 ml of ice-water. The aqueous phase was extracted twice more with methylene chloride. The organic phase was then washed successively with water, saturated sodium hydrogencarbonate and sodium chloride solution and filtered off with suction over neutral alumina. After concentrating, 21.5 g (72% of theory) of the title compound of m.p. 96–99° C. were obtained (active compound Example 1.020).

N-tert-Butyl-5-nitropyridine-2,3-dicarboximide

Half of 18 g (0.28 mol) of 98% strength nitric acid and, after 1 hour, the remainder were added in the course of 10 minutes with stirring at 20 to 25° C. to a suspension of 53.6 g (0.244 mol) of N-tert-butylpyridine-2,3-dicarboximide-1-oxide in 150 ml of glacial acetic acid and 71.4 g (0.7 mol) of acetic anhydride and the mixture was stirred at 25° C. for 16 hours. The reaction mixture was poured into 1.5 l of ice-water and extracted three times with 300 ml of methylene chloride each time. The organic extract was washed in succession with water, saturated sodium hydrogencarbonate and sodium chloride solution and dried over magnesium sulfate. After concentrating in vacuo, 55 g of a yellow syrup were obtained. This was flash-chromatographed on silica gel using methylene chloride and the middle fraction was concentrated (28 g).

This was initially introduced in 150 ml of 1,2-dichloroethane, treated with 28.9 g (0.213 mol) of phosphorus trichloride at 25° C. in the course of 10 minutes with stirring and stirred at 75° C. for 1½ hours. The reaction mixture was concentrated in vacuo, the residue was taken up in methylene chloride and the solution was stirred into ice-water. The organic phase was extracted in succession with water, saturated sodium hydrogencarbonate and sodium chloride solution and dried over magnesium sulfate. After filtering off with suction through neutral alumina, the filtrate was concentrated, and the residue was stirred with ether/pentane, filtered off with suction and dried. 20.5 g (33.7% of theory) of the title compound of m.p. 170–173° C. were obtained (active compound Example 1.021).

N-tert-Butyl-6-chloro-5-nitropyridine-2,3-dicarboximide 100 ml of phosphoryl chloride were treated with 7.5 g (0.028 mol) of N-tert-butyl-5-nitropyridine-2,3-dicarboximide-1-oxide at 60° C. and in portions in the course of 2 minutes with stirring and the mixture was stirred under reflux for 2 hours. The reaction mixture was concentrated under reduced pressure, the residue was taken up in methylene chloride and the solution was stirred into ice-water. The organic phase was extracted in succession with water, saturated sodium hydrogencarbonate and sodium chloride solution and dried. After filtering off with suction through neutral alumina, it was concentrated and the residue was stirred with ether and ether/pentane, filtered off with suction and dried. 4.49 g (56% of theory) of the title compound of m.p. 100–104° C. were obtained (active compound Example 1.019).

N-1-(Cyclopropyl)ethyl-6-amino-5-methylpyridine-2,3-dicarboximide 6.3 g (0.0254 mol) of N-1-(cyclopropyl)ethyl-6-fluoro-5-methylpyridine-2,3-dicarboximide and 4.1 g (0.051 mol) of potassium cyanate were introduced into a mixture of 50 ml of DMF and 1 ml of water at 25° C. with stirring and then stirred at 125° C. for 30 minutes. After concentrating the reaction mixture under reduced pressure, the residue was stirred in succession with methyl tert-butyl ether and with water. Insoluble matter was filtered off with suction, washed with methyl tert-butyl ether and dried under reduced pressure.

3.5 g (56% of theory) of the title compound of m.p. 219–220° C. were obtained. A further 1.6 g (=26% of theory) of the title compound of m.p. 201–219° C. were obtained from the organic phase after washing with water and drying over magnesium sulfate (active compound Example 1.059).

N-tert-Butyl-4-amino-6-chloropyridine- and 6-amino-4-chloropyridine-2,3-dicarboximide 14.3 g (0.052 mol) of N-tert-butyl 4,6-dichloropyridine-2,3-dicarboximide and 8.5 g (0.105 mol) of potassium cyanate were added to a mixture of 100 ml of DMF and 2 ml of water at 25° C. and the mixture was stirred at 125° C. for 20 minutes.

After concentrating the reaction mixture under reduced pressure, the residue was stirred into a mixture of methyl tert-butyl ether and water and the solid was filtered off with suction. Repeated stirring with methyl tert-butyl ether, filtering off with suction and drying yielded 8.73 g (66% of theory) of N-tert-butyl-4-amino-6-chloropyridine-2,3-dicarboximide of m.p. 232–234° C. (active compound Example 1.048).

The organic filtrate was washed with water and saturated sodium chloride solution, dried over magnesium sulfate and concentrated. The residue was taken up in methylene chloride and filtered off with suction through silica gel, 0.95 g (7.2% of theory) of N-tert-butyl-6-amino-4-chloropyridine-2,3-dicarboximide of m.p. 215–220° C. being isolated from fractions 3 and 4 (active compound Example 1.053).

According to these processes described in Examples B and the precursors, the pyridine-2,3-dicarboximides of the formula I listed in Table 1 were obtained. Novel pyridine-2,3-dicarboxylic anhydrides and pyridine-2,3-dicarboxylic acid esters are listed in Tables 2 and 3.

TABLE 1

[Structure I: pyrrolo-pyridine-dione with R1 on N, R2, R3, R4 on pyridine ring]

| No. | R¹ | R² | R³ | R⁴ | M.p. (° C.) |
|---|---|---|---|---|---|
| 1.001 | tert-C₄H₉ | CH₃ | NO₂ | H | 118–119 |
| 1.002 | i-C₃H₇ | CH₃ | NO₂ | H | 90–91 |
| 1.003 | tert-C₄H₉ | CH₃ | CH₃-C(O)-NH | H | 162–163 |
| 1.004 | tert-C₄H₉ | CH₃ | CF₃-C(O)-NH | H | 68–71 |
| 1.005 | tert-C₄H₉ | CH₃ | S=C=N— | H | 94–95 |
| 1.006 | tert-C₄H₉ | CH₃ | NH₂ | H | 242 |
| 1.007 | tert-C₄H₉ | Cl | NH₂ | Cl | |
| 1.008 | i-C₃H₇ | CH₃ | CF₃-C(O)-NH | H | 116–117 |
| 1.009 | i-C₃H₇ | CH₃ | NH₂ | H | 217–221 |
| 1.010 | i-C₃H₇ | CH₃ | S=C=N— | H | 78–80 |
| 1.011 | i-C₃H₇ | CH₃ | CH₃-C(O)-NH | H | 160–161 |
| 1.012 | 1-(Cyclopropyl)ethyl | CH₃ | S=C=N | H | 98–100 |
| 1.013 | 1-(Cyclopropyl)ethyl | CH₃ | CF₃-C(O)-NH | H | 64–65 |
| 1.014 | 1-(Cyclopropyl)ethyl | CH₃ | CH₃-C(O)-NH | H | 178–179 |
| 1.015 | 1-(Cyclopropyl)ethyl | CH₃ | NH₂ | H | 170–171 |
| 1.016 | 1-(Cyclopropyl)ethyl | CH₃ | NO₂ | H | $n_D^{23}$ = 1.5670 |
| 1.017 | i-C₃H₇ | CH₃ | CH₃SO₂NH | H | 158–160 |
| 1.018 | tert-C₄H₉ | CH₃ | CH₃SO₂NH | H | 149–153 |
| 1.019 | tert-C₄H₉ | Cl | NO₂ | H | 100–104 |
| 1.020 | 1-(Cyclopropyl)ethyl | H | NO₂ | H | 96–99 |
| 1.021 | tert-C₄H₉ | H | NO₂ | H | 170–173 |
| 1.022 | i-C₃H₇ | H | NO₂ | H | 166–169 |
| 1.023 | 1-(Cyclopropyl)ethyl | Cl | NO₂ | H | 65–66 |
| 1.024 | tert-C₄H₉ | H | CF₃-C(O)-NH | H | 142–145 |
| 1.025 | 1-(Cyclopropyl)ethyl | C₆H₅CH₂NH | H | H | 144–148 |
| 1.026 | tert-C₄H₉ | CH₃ | CH₃ | NH₂ | |
| 1.027 | 1-(Cyclopropyl)ethyl | CH₃ | CH₃ | NH₂ | |
| 1.028 | tert-C₄H₉ | CH₃ | CH₃ | NO₂ | |
| 1.029 | tert-C₄H₉ | CH₃ | CH₃ | OH | |

TABLE 1-continued

Structure I: pyrrolo-pyridine-dione with R¹ on N, R² at 2-position, R³ at 3-position, R⁴ at 4-position

| No. | R¹ | R² | R³ | R⁴ | M.p. (° C.) |
|---|---|---|---|---|---|
| 1.030 | tert-C₄H₉ | Cl | CH₃ | NH₂ | |
| 1.031 | 1-(Cyclopropyl)ethyl | CH₃ | Cl | NH₂ | |
| 1.032 | tert-C₄H₉ | CH₃O | Cl | NH₂ | |
| 1.033 | 1-(Cyclopropyl)ethyl | CH₃O | Cl | NH₂ | |
| 1.034 | tert-C₄H₉ | CH₃ | Cl | OH | |
| 1.035 | 1-(Cyclopropyl)ethyl | CH₃O | Cl | OH | |
| 1.036 | tert-C₄H₉ | Cl | Cl | NH₂ | 232–234 |
| 1.037 | 1-(Cyclopropyl)ethyl | Cl | Cl | NH₂ | |
| 1.038 | tert-C₄H₉ | Cl | Cl | CF₃(C=O)NH | |
| 1.039 | tert-C₄H₉ | CF₃—C(=O)—NH | CH₃ | H | 159–160 |
| 1.040 | tert-C₄H₉ | NH₂ | CH₃ | H | 286–290 |
| 1.041 | tert-C₄H₉ | NH₂ | CH₃O | H | 220–225 |
| 1.042 | tert-C₄H₉ | CF₃—C(=O)—NH | H | H | 151–154 |
| 1.043 | tert-C₄H₉ | H | CH₃—C(=O)—NH | H | 193–195 |
| 1.044 | tert-C₄H₉ | H | NH₂ | H | 187–190 |
| 1.045 | tert-C₄H₉ | CF₃—C(=O)—NH | Cl | H | 168–171 |
| 1.046 | tert-C₄H₉ | NH₂ | Cl | H | 258–260 |
| 1.047 | i-C₃H₇ | Cl | Cl | NH₂ | 249–253 |
| 1.048 | tert-C₄H₉ | Cl | H | NH₂ | 232–234 |
| 1.049 | tert-C₄H₉ | NH₂ | Cl | Cl | 215–220 |
| 1.050 | tert-C₄H₉ | CF₃—C(=O)—NH | CH₃O | H | 245–248 |
| 1.051 | i-C₃H₇ | Cl | CF₃—C(=O)—NH | H | 145–148 |
| 1.052 | tert-C₄H₉ | Cl | CF₃—C(=O)—NH | H | 124–127 |
| 1.053 | tert-C₄H₉ | NH₂ | H | Cl | 215–220 |
| 1.054 | tert-C₄H₉ | Cl | Cl | CF₃—C(=O)—NH | 135–137 |

TABLE 1-continued

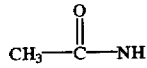

| No. | R₁ | R² | R³ | R⁴ | M.p. (° C.) |
|---|---|---|---|---|---|
| 1.055 | tert-C₄H₉ | Cl | H | CH₃—C(O)—NH | 136–139 |
| 1.056 | tert-C₄H₉ | Cl | H | CF₃—C(O)—NH | 105–106 |
| 1.057 | tert-C₄H₉ | Cl | CH₃O | NH₂ | 212–215 |
| 1.058 | 1-(Cyclopropyl)ethyl | CF₃—C(O)—NH | CH₃ | H | 170–172 |
| 1.059 | 1-(Cyclopropyl)ethyl | NH₂ | CH₃ | H | 219–220 |
| 1.060 | i-C₃H₇ | CH₃ | CH₃O—C(O)—NH | H | 174–175 |
| 1.061 | tert-C₄H₉ | CH₃O | CF₃—C(O)—NH | H | 185–187 |
| 1.062 | tert-C₄H₉ | CH₃O | CH₃—C(O)—NH | H | >280 |
| 1.063 | tert-C₄H₉ | CH₃O | NH₂ | H | 200–202 |
| 1.064 | tert-C₄H₉ | CH₃O | NO₂ | H | 140–141 |
| 1.065 | tert-C₄H₉ | NH₂ | H | H | 179–182 |
| 1.066 | i-C₃H₇ | NH₂ | H | H | 153–157 |
| 1.067 | i-C₃H₇ | NH₂ | CH₃ | H | 255–260 |
| 1.068 | i-C₃H₇ | CH₃O | NO₂ | H | 128–131 |
| 1.069 | 1-(Cyclopropyl)ethyl | CH₃O | NO₂ | H | 152–154 |
| 1.070 | tert-C₄H₉ | CH₃ | Cl | NH₂ | 2.20–221 |
| 1.071 | i-C₃H₇ | CH₃O | NH₂ | H | 213–214 |
| 1.072 | 1-(Cyclopropyl)ethyl | CH₃O | NH₂ | H | 163–165 |
| 1.073 | 1-(Cyclopropyl)ethyl | Cl | CH₃ | NH₂ | 236–238 |
| 1.074 | 1-(Cyclopropyl)ethyl | NH₂ | CH₃ | Cl | 234–236 |
| 1.075 | i-C₃H₇ | Cl | CH₃ | NH₂ | >305 |
| 1.076 | i-C₃H₇ | NH₂ | CH₃ | Cl | 298–302 |
| 1.077 | i-C₃H₇ | CH₃O | CF₃—C(O)—NH | H | 178–180 |
| 1.078 | 1-(Cyclopropyl)ethyl | CH₃O | CF₃—C(O)—NH | H | 134–136 |

TABLE 1-continued

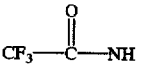

| No. | R¹ | R² | R³ | R⁴ | M.p. (° C.) |
|---|---|---|---|---|---|
| 1.079 | 1-(Cyclopropyl)ethyl | Cl | CH₃ | CF₃—C(=O)—NH | 162–163 |
| 1.080 | i-C₃H₇ | Cl | CH₃ | CF₃—C(=O)—NH | 155–157 |
| 1.081 | 1-(Cyclopropyl)ethyl | CF₃—C(=O)—NH | CH₃ | Cl | 81–83 |
| 1.082 | i-C₃H₇ | CF₃—C(=O)—NH | CH₃ | Cl | 111–114 |
| 1.083 | tert-C₄H₉ | Cl | CH₃ | NH₂ | 253–257 |
| 1.084 | tert-C₄H₉ | NH₂ | CH₃ | Cl | 215–217 |
| 1.085 | tert-C₄H₉ | Cl | CH₃ | CF₃—C(=O)—NH | 172–174 |
| 1.086 | tert-C₄H₉ | CF₃—C(=O)—NH | CH₃ | Cl | 85–88 |
| 1.087 | tert-C₄H₉ | Cl | NH₂ | H | 240–242 |
| 1.088 | tert-C₄H₉ | Cl | CF₃—C(=O)—NH | H | 144–147 |

TABLE 2

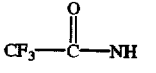

| No. | R² | R³ | R⁴ | Physical data - M.p. (° C.) ¹H-NMR, 200 MHz, δ [ppm] in CDCl₃ |
|---|---|---|---|---|
| 2.001 | H | NO₂ | H | 85–91 |
| 2.002 | Cl | NO₂ | H | |
| 2.003 | Cl | NO₂ | Cl | |
| 2.004 | CH₃ | NO₂ | H | CH₃: 3.05 (s/3), |

TABLE 2-continued

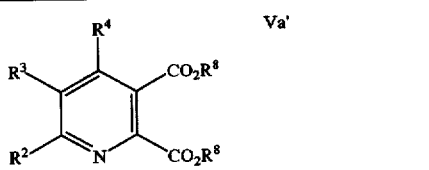

IIa'

| No. | $R^2$ | $R^3$ | $R^4$ | Physical data - M.p. (° C.) $^1$H-NMR, 200 MHz, δ [ppm] in CDCl$_3$ |
|---|---|---|---|---|
| | | | | Ar: 8.05 (s/1) |
| 2.005 | CH$_3$ | NO$_2$ | Cl | |
| 2.006 | H | NH$_2$ | H | |
| 2.007 | H | CF$_3$(C=O)NH | H | 153–156 |
| 2.008 | NH$_2$ | H | H | |
| 2.009 | C$_6$H$_5$—CH$_2$NH | H | H | |
| 2.010 | C$_6$H$_5$—CH$_2$—NH—C(=O)—CF$_3$ | H | H | 105–107 |
| 2.011 | CH$_3$O | NO$_2$ | H | 123–127 |
| 2.012 | CH$_3$O | NH$_2$ | H | |
| 2.013 | CH$_3$O | CF$_3$(C=O)NH | H | |
| 2.014 | CF$_3$(C=O)NH | H | H | |
| 2.015 | Cl | H | CH$_3$(C=O)NH | |

TABLE 3

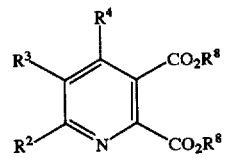

Va'

| No. | $R^2$ | $R^3$ | $R^4$ | $R^5$ | Physical data - M.p. (° C.) $^1$H-NMR, 270 MHz, δ [ppm] in CDCl$_3$ |
|---|---|---|---|---|---|
| 3.001 | H | NO$_2$ | H | C$_2$H$_5$ | $n_D^{25}$ = 1.5290 |
| 3.002 | Cl | NO$_2$ | H | CH$_3$ | 68–73 |
| 3.003 | Cl | NO$_2$ | Cl | C$_2$H$_5$ | |
| 3.004 | CH$_3$ | NO$_2$ | Cl | CH$_3$ | |
| 3.005 | H | NH$_2$ | H | C$_2$H$_5$ | Ar: 7.08 (d/1), 8.15 (d/1), NH$_2$: 4.45 (s/2) |
| 3.006 | H | CF$_3$(C=O)NH | H | C$_2$H$_5$ | $n_D^{25}$ = 1.5018 |
| 3.007 | NH$_2$ | H | H | CH$_3$ | |
| 3.008 | C$_6$H$_5$CH$_2$NH | H | H | C$_2$H$_5$ | 110–114 |
| 3.009 | C$_6$H$_5$CH$_2$ | Cl | H | C$_2$H$_5$ | |
| 3.010 | CH$_3$O | NO$_2$ | H | C$_2$H$_5$ | 60–64 |
| 3.011 | CH$_3$O | NH$_2$ | H | CH$_3$ | |
| 3.012 | CH$_3$O | CF$_3$(C=O)NH | H | CH$_3$ | |
| 3.013 | Cl | NH$_2$ | H | C$_2$H$_5$ | |
| 3.014 | NH | Cl | H | C$_2$H$_5$ | |
| 3.015 | CH$_3$O | H | NH$_2$ | CH$_3$ | |
| 3.016 | Cl | H | NH$_2$ | CH$_3$ | |
| 3.017 | Cl | NH$_2$ | H | CH$_3$ | 94–100 |
| 3.018 | CH$_3$O | NO$_2$ | H | CH$_3$ | 57–58 |
| 3.019 | NH$_2$ | H | H | C$_2$H$_5$ | 149–155 |
| 3.020 | Cl | NO$_2$ | H | C$_2$H$_5$ | 70–72 |
| 3.021 | Cl | NO$_2$ | H | CH$_3$ | Ar—CH$_3$ 8.78 (s/1) |
| 3.022 | CH$_3$ | NO$_2$ | H | CH$_3$ | 60–64 |

Use examples

It was possible to show the herbicidal action of the pyridine-2,3-dicarboximides of the formula I by greenhouse tests:

The cultivation containers used were plastic pots containing loamy sand containing approximately 3.0% of humus as a substrate. The seeds of the test plants were sown separately according to species.

In the case of pre-emergence treatment, the active compounds suspended or emulsified in water were applied immediately after sowing by means of finely dispersing nozzles. The containers were lightly watered in order to promote germination and growth and then covered with transparent plastic hoods until the plants had taken root. This covering causes uniform germination of the test plants if this has not been adversely affected by the active compounds.

For the purpose of post-emergence treatment, the test plants were first raised to a growth height of 3 to 15 cm depending on growth form and only then treated with the active compounds suspended or emulsified in water. For this purpose, the test plants were either sown directly and then raised in the same containers or they were first raised separately as seed plants and transplanted into the test containers a few days before treatment. The application rate for post-emergence application was 0.5 or 0.25 kg/ha of a.s.

The plants were kept species-specifically at from 10–25° C. or 20–35° C. The test period extended over 2 to 4 weeks. During this time, the plants were tended and their reaction to the individual treatments was assessed.

The herbicidal action was graded on a scale of from 0 to 100. 100 in this case means no emergence of the plants or complete destruction of at least the above-ground parts and 0 means no damage or normal course of growth.

The plants used in the greenhouse tests were made up of the following species:

| Abbreviation | Botanical name | Common name |
|---|---|---|
| CHEAL | *Chenopodium album* | Common lamb's-quarters |
| POLPE | *Polygonum persicaria* | Lady's-thumb |
| SOLNI | *Solanum nigrum* | Black nightshade |

The results (see following Table I) show the superior herbicidal action of the compounds according to the invention compared with the comparison Example A known from EP-A 422 456.

TABLE I

Examples of the control of undesired plants on post-emergence application of 0.5 kg and 0.25 kg of a.s./ha in a greenhouse

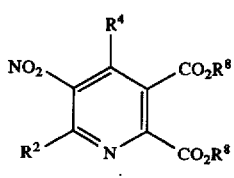

| $R^3$ | $NH_2$ | $NH_2$ | H | H |
|---|---|---|---|---|
| $R^2$ | $CH_3$ | $CH_3$ | $CH_3$ | $CH_3$ |
| Ex. No. | 1.015 | 1.015 | A | A |
| Application rate (kg of a.s./ha) | 0.5 | 0.25 | 0.5 | 0.25 |
| Test plants | Damage in % | | | |
| CHEAL | 100 | 90 | 100 | 75 |
| POLPE | 100 | 100 | 100 | 60 |
| SOLNI | 100 | 100 | 90 | 10 |

We claim:

1. A process for preparing nitro-substituted pyridinedicarboxylic acid diesters of the formula Vb Vb where each of $R^2$ and $R^4$ is a member selected from the group consisting of I) hydrogen;

ii) halogen, nitro or cyano;

iii) $C_1$–$C_6$-alkyl, which can be substituted by one to five halogen atoms and/or one or two of the following radicals: $C_1$–$C_4$-alkoxy, $C_1$–$C_4$-haloalkoxy, $C_1$–$C_4$-alkylthio, $C_1$–$C_4$-haloalkylthio, $C_3$–$C_6$-cycloalkyl or cyano;

iv) benzyl which can be substituted up to three times by $C_1$–$C_4$-alkyl, $C_1$–$C_4$haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro;

v) $C_3$–$C_8$-cycloalkyl which can be substituted one to three times by $C_1$–$C_4$-alkyl or halogen;

vi) $C_2$–$C_8$-alkenyl which can be substituted up to three times by halogen and/or once by $C_1$–$C_3$-alkoxy or by phenyl which can carry one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$alkylthio, $C_1$–$C_4$-haloalkylthio, halogen, cyano or nitro;

vii) $C_2$–$C_6$-alkynyl which can be substituted up to three times by halogen or $C_1$–$C_3$alkoxy and/or once by phenyl which can carry one to three of the following groups:

$C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro;

viii) $C_1$–$C_4$-alkoxy, $C_1$–$C_4$-alkylthio, $C_1$–$C_4$-haloalkoxy, $C_1$–$C_4$-haloalkylthio, $C_2C_5$-alkenyloxy, $C_2$–$C_5$-alkynyloxy, $C_1$–$C_4$-alakylsulfinyl, $C_1$–$C_4$-alkylsulfonyl, $C_1$–$C_4$-haloalkylsulfonyl, ix) phenoxy or phenylthio which can be substituted up to three times by $C_1$–$C_4$-alkyl, $C_1$–$C_4$-halolalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro;

x) a 5- or 6-membered heterocyclic radical having one or two heteroatoms selected from the group consisting of oxygen, sulfur and nitrogen which can carry one or two of the following groups: $C_1$–$C_3$-alkyl, halogen, $C_1$–$C_3$-alkoxy or $C_2$–$C_4$alkoxycarbonyl;

xi) phenyl which can carry one to three of the following groups: $C_1$–$C_6$-alkyl, $C_1$–$C_6$-haloalkyl, $C_1$–$C_6$-alkoxy, $C_1$–$C_4$-haloalkoxy, $C_1$–$C_6$-alkylthio, $C_1$–$C_6$-haloalkylthio, halogen, nitro or cyano;

xii) a group $OR^5$, where $R^5$ is hydrogen, $C_1$–$C_4$-alkylcarbonyl, $C_1$–$C_4$haloalkylcarbonyl, $C_1$–$C_4$-alkoxycarbonyl, $C_1$–$C_4$-alkoxy-$C_2$–$C_4$-alkoxycarbonyl, $C_1$–$C_4$-alkylcarbamoyl, $C_1$–$C_4$adialkylcarbamoyl, $C_1$–$C_4$-alkylsulfonyl. $C_1$–$C_4$haloalkylsulfonyl, sulfamoyl, $C_1$–$C_4$-alkylaminosulfonyl, $C_1$–$C_4$-dialkylaminosulfonyl, phenylsulfonyl, which can be substituted one to three times by $C_1$–$C_4$-alkyl, $C_1$–Cd-haloalkyl, $C_1$–$C_4$-alkoxy, $C_1$–$C_4$-haloalkoxy, $C_1$–$C_4$-alkylthio, halogen, cyano or nitro;

xiii) a group $NR^6R^7$, where $R^6$ is hydrogen, $C_1$–$C_4$-alkyl, benzyl, $C_1$–$C_4$-alkoxy or, together with $R^7$ is C=S and $R^7$ is hydrogen, $C_1$–$C_4$-alkyl, $C_1$–Cadalkylcarbonyl, $C_1$–$C_4$-haloalkylcarbonyl, $C_1$–$C_4$-alkoxycarbonyl, $C_1$–$C_4$alkoxy-$C_1$–$C_4$-alkoxycarbonyl, C,-$C_4$-alkylcarbamoyl, $C_1$–C4dialkylcarbamoyl, $C_1$–$C_4$-alkylsulfonyl, $C_1$–$C_4$-haloalkylsulfonyl, sulfamoyl, $C_1$–$C_4$-alkylaminosulfonyl, $C_1$–$C_4$-dialkylaminosulfonyl, phenylsulfonyl, which can be substituted one to three times by $C_1$–$C_4$-alkyl, $C_1$–$C_4$ haloalkyl, $C_1$–Cad,-alkoxy, $C_1$–$C_4$-haloalkoxy, $C_1$–$C_4$-alkylthio, halogen, cyano or nitro; and $R^8$ is an unsubstituted or substituted low molecular weight alkyl, alkynyl radical, which comprises treating the N-oxides of pyridine-2,3-dicarboxylic acid esters of the formula Vb'

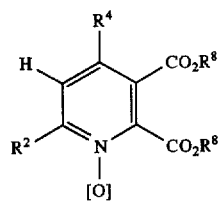

Vb' with a a member selected from the group consisting of nitric acid, sodium nitrate in the presence of acetic acid or trifluoroacetic acid, or nitric acid mixed with sulfuric acid, phosphoric acid, glacial acetic acid or liquid hydrogen fluoride and then removing the N-oxide group.

2. A pyridine-2,3-dicarboxylic acid diester of the formula Vb

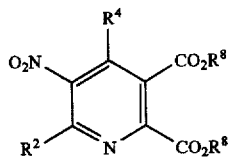

Vb where $R^2$, $R^6$ and $R^7$ have the meanings mentioned in claim 1, $R^4$ is hydrogen, chloro, cyano, $C_1$–$C_6$-alkyl, $C_1$–$C_4$-alkoxy, phenoxy or $NR^6R^7$, and $R^8$ is a $C_1$–$C_4$-alkyl, $C_3$–$C_5$-alkenyl or $C_3$–$C_5$-alkynyl radical, which may be substituted by halogen, phenyl or $C_1$–$C_4$-alkoxy, with the proviso that $R^4$ is hydrogen only when $R^2$ is hydrogen.

3. A pyridine-2,3-dicarboxylic acid diester of the formula Vd

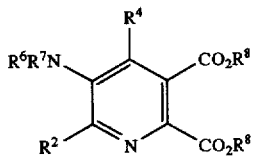

Vd where the radicals $R^2$ $R^4$, $R^6$, $R^7$ and $R^8$ are defined as recited in claim 1, excluding diethyl and dimethyl 5-amino-6-methyl-pyridine-2,3- dicarboxylate, diethyl 5,6-diaminopyridine-2,3-dicarboxylate, diethyl 5-acetamido-6-methylpyridine-2,3-dicarboxylate, diethyl 5-methylaminoa6-methylpyridine-2,3-dicarboxylate, and diethyl-5-(N,N-acetyl methyl)amino-6-methyl-pyridine-2,3-dicarboxylate.

* * * * *

UNITED STATES PATENT AND TRADEMARK OFFICE
CERTIFICATE OF CORRECTION

PATENT NO. : 5,959,116
DATED : September 28, 1999
INVENTOR(S) : HAMPRECHT et al.

It is certified that error appears in the above-identified patent and that said Letters Patent is hereby corrected as shown below:

On the cover sheet insert the following priority information:
--[30]  Foreign Application Priority Data
  Dec. 22, 1993  [DE]  Germany ........... P 43 43 922.5--.

Col. 52, claim 1, line 27, "$C_1$-$C_4$-alakylsulfinyl" should be --$C_1$-$C_4$-alkylsulfinyl--.
Col. 52, claim 1, line 37, "$C_2$-$C_4$alkoxycarbonyl" should be --$C_2$-$C_4$-alkoxycarbonyl--.
Col. 52, claim 1, line 40, "$C_1$-$C_4$-haloalkoxy" should be --$C_1$-$C_6$-haloalkoxy--.
Col. 52, claim 1, line 43, "$C_1$-$C_4$haloalkylcarbonyl" should be --$C_1$-$C_4$-haloalkylcarbonyl--.
Col. 52, claim 1, line 46, "$C_1$-$C_4$adialkylcarbamoyl" should be --$C_1$-$C_4$-dialkylcarbamoyl--.
Col. 52, claim 1, line 47, "$C_1$-$C_4$haloalkylsulfonyl" should be --$C_1$-$C_4$-haloalkylsulfonyl--.
Col. 52, claim 1, line 50, "$C_1$-Cd-haloalkyl" should be --$C_1$-$C_4$-haloalkyl--.
Col. 52, claim 1, line 56, "$C_1$-Cadalkylcarbonyl" should be --$C_1$-$C_4$-alkylcarbonyl--.
Col. 52, claim 1, line 57, "$C_1$-$C_4$-alkoxy-$C_1$-$C_4$-" should be --$C_1$-$C_4$-alkoxy-$C_2$-$C_4$- --.
Col. 52, claim 1, line 58, "$C$,-$C_4$-alkylcarbamoyl" should be --$C_1$-$C_4$-alkylcarbamoyl--.
Col. 52, claim 1, line 59, "$C_1$-C4dialkylcarbamoyl" should be --$C_1$-$C_4$-dialkylcarbamoyl--.
Col. 52, claim 1, line 63, "$C_1$-Cad,-" should be --$C_1$-$C_4$- --.
Col. 53, claim 1, line 14, delete "a a" and substitute --a--.
Col. 54, claim 3, line 21, after "$R^2$" insert a comma --,--.
Col. 54, claim 3, line 26, delete "5-methylaminoa6-" and substitute --5-methylamino-6- --.
Col. 54, claim 3, line 27, after "acetyl" insert a comma --,--.

Signed and Sealed this

Twenty-fifth Day of July, 2000

Attest:

Q. TODD DICKINSON

*Attesting Officer*  *Director of Patents and Trademarks*